US009023845B2

(12) United States Patent
Lingwood et al.

(10) Patent No.: US 9,023,845 B2
(45) Date of Patent: May 5, 2015

(54) COMPOSITIONS AND METHODS FOR TREATING LYSOSOMAL DISORDERS

(75) Inventors: Clifford A. Lingwood, Toronto (CA); Michael S. McGrath, Burlingame, CA (US); Arasteh Ari Azhir, Los Altos, CA (US)

(73) Assignees: Neuraltus Pharmaceuticals, Inc., Palo Alto, CA (US); The Hospital for Sick Children (CA)

( * ) Notice: Subject to any disclaimer, the term of this patent is extended or adjusted under 35 U.S.C. 154(b) by 298 days.

(21) Appl. No.: 13/551,395

(22) Filed: Jul. 17, 2012

(65) Prior Publication Data

US 2013/0012539 A1 Jan. 10, 2013

Related U.S. Application Data

(63) Continuation of application No. 12/324,759, filed on Nov. 26, 2008, now Pat. No. 8,252,789.

(60) Provisional application No. 60/991,136, filed on Nov. 29, 2007, provisional application No. 61/095,825, filed on Sep. 10, 2008.

(51) Int. Cl.
| A61K 31/535 | (2006.01) |
| A61K 31/41 | (2006.01) |
| A61K 31/445 | (2006.01) |
| A61K 45/06 | (2006.01) |

(52) U.S. Cl.
CPC .............. *A61K 31/41* (2013.01); *A61K 31/445* (2013.01); *A61K 45/06* (2013.01)

(58) Field of Classification Search
CPC ...... A61K 31/41; A61K 31/445; A61K 45/06
USPC ........................................................ 514/232.2
See application file for complete search history.

(56) References Cited

U.S. PATENT DOCUMENTS

| 5,103,002 | A | 4/1992 | Wieland |
| 5,656,641 | A | 8/1997 | Platt et al. |
| 5,700,826 | A | 12/1997 | Mjalli et al. |
| 5,780,228 | A | 7/1998 | Parma et al. |
| 5,801,185 | A | 9/1998 | Platt et al. |
| 5,840,721 | A | 11/1998 | Mjalli et al. |
| 6,888,015 | B2 | 5/2005 | Kobayashi et al. |
| 7,253,185 | B2 | 8/2007 | Shayman et al. |
| 8,252,789 | B2 | 8/2012 | Lingwood et al. |
| 2001/0031741 | A1 | 10/2001 | Ziegler et al. |
| 2002/0095135 | A1 | 7/2002 | Meeker et al. |

(Continued)

FOREIGN PATENT DOCUMENTS

| GB | 2466912 B | 1/2012 |
| WO | WO 86/07054 A1 | 12/1986 |

(Continued)

OTHER PUBLICATIONS

U.S. Appl. No. 12/853,938, filed Aug. 10, 2010, McGrath et al.

(Continued)

*Primary Examiner* — San-Ming Hui
(74) *Attorney, Agent, or Firm* — Wilson Sonsini Goodrich & Rosati

(57) ABSTRACT

The present invention provides compositions and methods for treating lysosomal disorders using a class of substituted imidazole derivatives or compounds.

19 Claims, 4 Drawing Sheets

(56) References Cited

U.S. PATENT DOCUMENTS

| | | |
|---|---|---|
| 2003/0087868 A1 | 5/2003 | Yew et al. |
| 2003/0092736 A1 | 5/2003 | Cheng et al. |
| 2003/0095953 A1 | 5/2003 | Cabot et al. |
| 2005/0245735 A1 | 11/2005 | Defrees |
| 2007/0072916 A1 | 3/2007 | Shayman |
| 2007/0203215 A1 | 8/2007 | Newman et al. |

FOREIGN PATENT DOCUMENTS

| | | |
|---|---|---|
| WO | WO 2004/016086 A2 | 2/2004 |
| WO | WO 2004/016086 A3 | 4/2004 |
| WO | WO 2005/013947 A2 | 2/2005 |
| WO | WO 2005/013947 A3 | 4/2005 |
| WO | WO 2007/064091 A1 | 6/2007 |
| WO | WO 2008/105565 A1 | 9/2008 |

OTHER PUBLICATIONS

De Rosa, et al. Role of multiple drug resistance protein 1 in neutral but not acidic glycosphingolipid biosynthesis. J Biol Chem. Feb. 27, 2004;279(9):7867-76.

European office action dated Mar. 6, 2012 for Application No. 08857408.2.

European search report and search opinion dated Jan. 11, 2011 for Application No. 08857408.2.

International search report dated Mar. 4, 2009 for PCT Application No. US2008/85039.

Lala, et al. Retroviral transfection of Madin-Darby canine kidney cells with human MDR1 results in a major increase in globotriaosylceramide and 10(5)- to 10(6)-fold increased cell sensitivity to verocytotoxin. Role of p-glycoprotein in glycolipid synthesis. J Biol Chem. Mar. 3, 2000;275(9):6246-51.

Mattocks, et al. Treatment of neutral glycosphingolipid lysosomal storage diseases via inhibition of the ABC drug transporter, MDR1. Cyclosporin A can lower serum and liver globotriaosyl ceramide levels in the Fabry mouse model. FEBS Lett. 2006; 273(9):2064-2075.

Moyses, C. Substrate reduction therapy: clinical evaluation in type 1 Gaucher disease. Philos Trans R Soc Lond B Biol Sci. May 29, 2003;358(1433):955-60.

Pastores. Miglustat: substrate reduction therapy for lysosomal storage disorders associated with primary central nervous system involvement. Recent Pat CNS Drug Discov. Jan. 2006;1(1):77-82.

Sarshar, et al. 2,4,5-Trisubstituted imidazoles: novel nontoxic modulators of P-glycoprotein mediated multidrug resistance. Part 1. Bioorg Med Chem Lett. Dec. 4, 2000;10(23):2599-601.

Stricklett, et al. Inhibition of p38 mitogen-activated protein kinase ameliorates cytokine up-regulated shigatoxin-1 toxicity in human brain microvascular endothelial cells. J Infect Dis. Feb. 1, 2005;191(3):461-71. Epub Dec. 22, 2004.

Newman, et al. OC144-093, a novel P glycoprotein inhibitor for the enhancement of anti-epileptic therapy. Novartis Found Symp. 2002;243:213-26; discussion 226-30, 213-235.

Sankatsing, et al. P glycoprotein in human immunodeficiency virus type 1 infection and therapy. Antimicrob Agents Chemother. Apr. 2004;48(4):1073-81.

control Fabry mice | Formula 2 treated Fabry mice | CsA treated Fabry mice

COMPOSITIONS AND METHODS FOR TREATING LYSOSOMAL DISORDERS

RELATED APPLICATIONS

This application is a continuation application of U.S. Ser. No. 12/324,759, filed Nov. 26, 2008, now U.S. Pat. No. 8,252,789, issued on Aug. 28, 2012, which claims the benefit of U.S. Provisional Patent Application No. 60/991,136, filed Nov. 29, 2007, and U.S. Provisional Patent Application No. 61/095,825, filed Sep. 10, 2008, the disclosures of which are herein incorporated by reference in their entirety.

STATEMENT AS TO FEDERALLY SPONSORED RESEARCH

The present invention was made with the support of the Canadian government under Grant number MT 13073 by the Canadian Institutes of Health Research.

BACKGROUND

Glycosphingolipid (GSL) levels affect a variety of cell functions, such as growth, differentiation, adhesion between cells or between cells and matrix proteins, binding of microorganisms and viruses to cells, and metastasis of tumor cells. Glycosphingolipids (GSLs) are derived from glucosylceramide (GlcCer), and the GlcCer precursor, ceramide. GSLs and their precursors have a role in the differentiation or inhibition of cell growth (Bielawska, et al., *FEBS Letters* 307-211-214 (1992)) and may be involved in functioning of vitamin $D_3$, tumor necrosis factor $\alpha$, interleukins, and apoptosis (programmed cell death). The sphingols (sphingoid bases), precursors of ceramide, and products of ceramide catabolism, have also been shown to influence many cell systems, possibly by inhibiting protein kinase C (PKC).

Glucosylceramide is made on the outler leaflet of the Golgi through the action of GlcCer synthase. GlcCer is thought to be then transferred to the lumen of the Golgi for glycotransferases to be able to access GlcCer to generate more complex GSLs. The ABC transporter, multiple drug resistance protein 1 (MDR1, P-glycoprotein) is believed to promote GSL synthesis. MDR1 has been shown to translocate glucosylcermide from the cytosolic to the luminal Golgi surface.

The importance of GSL metabolism is underscored by the seriousness of disorders resulting from defects in GSL metabolizing enzymes. For example, Tay-Sachs, Gaucher's, and Fabry's diseases, resulting from enzymatic defects in the GSL degradative pathway and the accumulation of GSL in the patient, all have severe clinical manifestations. Another example of the importance of GSL function is seen in a mechanism by which blood cells, whose surfaces contain selectin, can, under certain conditions, bind to GSLs in the blood vessel walls and produce acute, life-threatening inflammation (Alon et al., *J. Immunol.*, 54:5356-5366 (1995)).

Because of the significant impact GSLs have on several biochemical processes, there remains a need for compounds to modulate GSL synthesis and metabolism when the processes become awry, resulting in diseases and disorders. Thus, it is desirable to provide compounds and therapeutic methods to treat conditions and diseases associated with altered GSL levels and/or GSL precursor levels. The present invention provides compositions and methods that satisfies these needs and provides related advantages as well.

SUMMARY

The present invention provides methods and compositions for reducing glycolipid synthesis in a subject suffering from a disease other than cancer comprising administering to the subject an effective amount of a compound of Formula 1

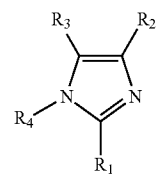

Formula 1 in the form of a free compound or its pharmaceutically acceptable pro-drug, metabolite, analogue, derivative, solvate or salt wherein the substituents $R_1$, $R_2$, $R_3$, and $R_4$ are defined as described in (a) and (b) below:

(a) when $R_1$ is selected from the group consisting of:
  substituted $C_{1-11}$ alkyl or substituted $C_{2-11}$ alkenyl, wherein the substituents are selected from the group consisting of hydroxy, $C_{1-6}$ alkyloxy; or
  (ii) mono-, di-, and tri-substituted aryl-$C_{0-11}$ alkyl wherein aryl is selected from the group consisting of phenyl, furyl, thienyl wherein the substituents are selected from the group consisting of:
    (a) phenyl, trans-2-phenylethenyl, 2-phenylethynyl, 2-phenylethyl, wherein the said phenyl group is mono- or disubstituted with a member selected from the group consisting of hydroxy, halo, $C_{1-4}$ alkyl and $C_{1-4}$ alkyloxy,
    (b) substituted $C_{1-6}$ alkyl, substituted $C_{2-6}$ alkyloxy, substituted $C_{2-6}$ alkylthio, substituted $C_{2-6}$ alkoxycarbonyl, wherein the substituents are selected from the group consisting of $C_{1-6}$ alkoxy, and $C_{1-6}$ alkylthio; and
    (c) $C_{1-11}$ $CO_2R_5$, $C_{1-11}CONHR_5$, trans-$CH=CHCO_2R_5$, or trans-$CH=CHCONHR_5$ wherein $R_5$ is $C_{1-11}$ alkyl, or phenyl $C_{1-11}$ alkyl, $C_{1-6}$ alkoxycarbonylmethyleneoxy;
then $R_2$ and $R_3$ are each independently selected from the group consisting of mono-, di, and tri-substituted phenyl wherein the substituents are independently selected from:
  (i) substituted $C_{1-6}$ alkyl,
  (ii) substituted $C_{1-6}$ alkyloxy, $C_{3-6}$ alkenyloxy, substituted $C_{3-6}$ alkenyloxy,
  (iii) substituted $C_{1-6}$ alkyl-amino, di(substituted $C_{1-6}$ alkyl) amino,
  (iv) $C_{3-6}$ alkenyl-amino, di($C_{3-6}$ alkenyl)amino, substituted $C_{3-6}$ alkenyl-amino, di(substituted $C_{3-6}$ alkenyl)amino,
  (v) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl) piperazino, 4-N—($C_{1-6}$ alkylamino $C_{1-6}$ alkyl)piperazino, 4-N—($C_{1-6}$ alkylamino $C_{3-6}$ alkenyl)piperazino, wherein the substituents are selected from the group consisting of:
  (a) hydroxy, $C_{1-6}$ alkylalkoxy, $C_{1-6}$ alkylamino
  (b) $C_{3-6}$ alkenyloxy, C3-6 alkenylamino, or
  (c) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl) piperazino, 4-N—($C_{1-6}$ alkylamino $C_{1-6}$ alkyl)piperazino, 4-N—($C_{1-6}$ alkylamino $C_{3-6}$ alkenyl)piperazino, or $R_2$ and $R_3$ taken together forming an aryl group or substituted aryl, wherein the substituents are defined as above in (i)-(v);

and $R_4$ is selected from the group consisting of:
  (i) hydrogen;
  (ii) substituted $C_{1-11}$ alkyl or $C_{2-11}$ alkenyl wherein the substituents are independently selected from the group consisting of hydrogen, hydroxy, $C_{1-6}$ alkyloxy, $C_{1-6}$ alkylthio, $C_{1-6}$ alkylamino, phenyl-$C_{1-6}$ alkylamino, $C_{1-6}$ alkoxycarbonyl; or
  (iii) substituted aryl $C_{0-11}$ alkyl wherein the aryl group is selected from phenyl, imidazolyl, furyl, thienyl in which the substituents are selected from A(a-c); or (b) when $R_1$ is selected from the group consisting of:

Mono-, di-, and tri-substituted aryl-$C_{0-6}$ alkyl wherein aryl is selected from the group consisting of phenyl, thienyl, and the substituents are selected from the group consisting of
  (a) trans-2-substituted benzimidazolylethenyl, trans-2-substituted benzoxazolylethenyl, trans-2-substituted benzthiazolylethenyl, in which the substituents are selected from the group consisting of hydrogen, hydroxy, halo, trihalomethyl, $C_{1-4}$ alkyl and $C_{1-4}$ alkyloxy, $C_{1-4}$ alkyloxycarbonyl, $C_{1-4}$ alkylamino, alkyl)amino, $C_{3-6}$ alkenylamino, di($C_{3-6}$ alkenyl)amino, $C_{1-4}$ alkyloxy-$C_{1-4}$ alkylamino, substituted $C_{1-4}$ alkyl and $C_{1-4}$ alkyloxy, substituted $C_{1-4}$ alkyloxycarbonyl, substituted $C_{1-4}$ alkylamino, di(substituted $C_{1-4}$ alkyl)amino, substituted $C_{3-6}$ alkenylamino, di(substituted $C_{3-6}$ alkenyl)amino, wherein the substituents are as defined above,
  (b) trans-2-cyano ethenyl, trans-2-alkylsulfonyl ethenyl, trans-2-alkenylsulfonyl ethenyl, trans-2-substituted alkylsulfonyl ethenyl, trans-2-substituted alkenylsulfonyl ethenyl, in which the substituents are defined above,
  (c) $C_{1-6}$ $CO_2R_5$, trans-CH=CHCO$_2R_5$, $C_{1-6}$CONHR$_5$, or trans-CH=CHCONHR$_5$, wherein $R_5$ is $C_{1-6}$ alkoxy $C_{2-6}$ alkyl, amino $C_{2-6}$ alkyl, $C_{1-6}$ alkylamino $C_{2-4}$ alkyl, di($C_{1-6}$ alkyl)amino $C_{2-6}$ alkyl, $C_{1-6}$ alkylthio $C_{2-6}$ alkyl, substituted $C_{1-6}$ alkoxy $C_{2-6}$ alkyl, substituted $C_{1-6}$ alkylamino $C_{2-6}$ alkyl, di(substituted $C_{1-6}$ alkyl)amino $C_{2-6}$ alkyl, substituted $C_{1-6}$ alkylthio $C_{2-6}$ alkyl, in which the substituents are selected from the group consisting of pyrrolidino, piperidino morpholino, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-4}$ alkoxy $C_{3-6}$ alkenyl)piperazino, 4-N—($C_{1-4}$ alkylamino $C_{1-6}$ alkyl)piperazino, 4-N—($C_{1-6}$ alkylamino $C_{3-6}$ alkenyl)piperazino, imidazolyl, oxazolyl, thiazolyl,
  (d) $C_{1-6}$CONR$_6$R$_7$, or trans-CH=CHCONR$_6$R$_7$, wherein $R_6$ and $R_7$ are independently selected from the group consisting of $C_{1-6}$ alkyl, phenyl $C_{1-6}$ alkyl, $C_{1-6}$ alkoxycarbonylmethyleneoxy, hydroxy $C_{2-6}$ alkyl, $C_{1-6}$ alkyloxy $C_{2-6}$ alkyl, amino $C_{2-6}$ alkyl, $C_{1-6}$ alkylamino $C_{2-6}$ alkyl, di($C_{1-6}$ alkyl)amino $C_{2-4}$ alkyl, $C_{1-6}$ alkylthio $C_{2-6}$ alkyl, substituted $C_{1-6}$ alkoxy $C_{2-6}$ alkyl, substituted $C_{1-6}$ alkylamino $C_{2-6}$ alkyl, di(substituted $C_{1-6}$ alkyl)amino $C_{2-6}$ alkyl, substituted $C_{1-6}$ alkylthio $C_{2-6}$ alkyl, wherein the substituents are selected from the group consisting of pyrrolidino, piperidino, morpholino, piperazino, 4-N—$C_{1-6}$ alkylpiperazino, 4-N—$C_{3-4}$ alkenylpiperazino, 4-N—($C_{1-6}$ alkoxy $C_{1-4}$ alkyl)piperazino, 4-N—($C_{1-6}$ alkoxy $C_{3-6}$ alkenyl)piperazino, 4-N—($C_{1-6}$ alkylamino $C_{1-6}$ alkyl)piperazino, 4-N—($C_{1-6}$ alkylamino $C_{3-6}$ alkenyl)piperazino, imidazolyl, oxazolyl, thiazolyl,
  (e) $R_7$C(O)$C_{1-6}$ alkyl, $R_7$C(O)$C_{2-6}$ alkenyl, in which $R_7$ is defined as above [2(d)],
  (f) HO—$C_{1-6}$ alkyl-$C_{2-6}$ alkenyl, $R_7$—O—$C_{1-6}$ alkyl-$C_{2-6}$ alkenyl, $R_7$NH—$C_{1-6}$ alkyl-$C_{2-6}$ alkenyl, $R_6R_7$N—$C_{1-6}$ alkyl-$C_{2-6}$ alkenyl, $R_7$NH—C(O)—O—$C_{1-6}$ alkyl-$C_{2-6}$ alkenyl, $R_6R_7$N—C(O)—O—$C_{1-6}$ alkenyl, $R_7$O—C(O)—O—$C_{1-6}$ alkyl-$C_m$ alkenyl, $R_7$—C(O)—O—$C_{1-6}$ alkyl-$C_{2-6}$ alkenyl, wherein $R_6$ and $R_7$ is defined as above [2(d)],
  (g) $R_7$—O—$C_{0-3}$ alkyl-$C_{3-6}$ cycloalkan-1-yl, $R_7$NH—$C_{0-3}$ alkyl-$C_{3-6}$ cycloalkan-1-yl, $R_6R_7$N—$C_{0-3}$ alkyl-$C_{3-6}$ cycloalkan-1-yl, $R_7$NH—C(O)—O—$C_{0-3}$ $C_{3-6}$ cycloalkan-1-yl, $R_6R_7$N—C(O)—O—$C_{0-3}$ alkyl-$C_{3-6}$ cycloalkan-1-yl, $R_7$O—C(O)—O—$C_{0-3}$ alkyl-$C_{3-6}$ cycloalkan-1-yl, $R_7$—C(O)—O—$C_{0-3}$ alkyl-$C_{3-6}$ cycloalkan-1-yl, $R_7$O—C(O)—Co-3 alkyl-$C_{3-6}$ cycloalkan-1-yl, wherein $R_7$ and is defined as above [B(d)];

then $R_2$ and $R_3$ are each independently selected from the group consisting of:
(1) hydrogen, halo, trihalomethyl, $C_{1-6}$ alkyl, substituted $C_{1-6}$ alkyl, $C_{2-6}$ alkenyl, substituted $C_{1-6}$ alkenyl, $C_{1-6}$ alkyloxy, substituted $C_{1-6}$ alkyloxy, $C_{3-6}$ alkenyloxy, substituted $C_{3-6}$ alkenyloxy, $C_{1-6}$ alkylamino, substituted $C_{1-6}$ alkylamino, $C_{3-6}$ alkenylamino, substituted $C_{3-6}$ alkenylamino,
(2) mono-, di-, and tri-substituted phenyl wherein the substituents are independently selected from:
  (i) halo, trifluoromethyl, substituted $C_{1-6}$ alkyl,
  (ii) $C_{1-6}$ alkyloxy, substituted $C_{1-6}$ alkyloxy, $C_{3-6}$ alkenyloxy, substituted $C_{3-6}$ alkenyloxy,
  (iii) $C_{1-6}$ alkyl-amino, di($C_{1-6}$ alkyl)amino, substituted $C_{1-6}$ alkyl-amino, di(substituted $C_{1-6}$ alkyl)amino, $C_{3-6}$ alkenyl-amino, di($C_{3-6}$ alkenyl)amino, substituted $C_{3-6}$ alkenyl-amino, di(substituted $C_{3-6}$ alkenyl)amino, or
  (iv) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl) piperazino, 4-N—($C_{1-6}$ alkylamino $C_{1-6}$ alkyl)piperazino, 4-N—($C_{1-6}$ alkylamino $C_{3-6}$ alkenyl)piperazino, wherein the substituents are selected from the group consisting of:
    (a) hydrogen, hydroxy, halo, trifluoromethyl,
    (b) $C_{1-6}$ alkylalkoxy, $C_{1-6}$ alkylamino, $C_{1-6}$ alkylthio,
    (c) $C_{3-6}$ alkenyloxy, $C_{3-6}$ alkenylamino, $C_{3-6}$ alkenylthio, or
    (d) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl) piperazino, 4-N—($C_{1-6}$ alkylamino $C_{1-6}$ alkyl)piperazino, 4-N—($C_{1-6}$ alkylamino $C_{3-6}$ alkenyl)piperazino;

with the proviso that at least one of $R_2$ and $R_3$ group be selected from [B (2)] and the phenyl and the substituents be selected from (ii)-(v) above; or $R_2$ and $R_3$ taken together forming an aryl group such as phenyl, pyridyl, in which the aryl may be optionally substituted, wherein the substituents are defined as above in (i)-(iv);

and $R_4$ is selected from the group consisting of:
  (a) hydrogen;
  (b) substituted $C_{1-11}$ alkyl or $C_{2-11}$ alkenyl wherein the substituents are independently selected from the group consisting of:
    (i) hydrogen, hydroxy, $C_{1-6}$ alkyloxy, $C_{1-6}$ alkylthio, $C_{1-6}$ alkylamino, phenyl-$C_{1-6}$ alkylamino, $C_{1-6}$ alkoxycarbonyl;
    (ii) substituted $C_{1-6}$ alkyloxy, $C_{3-6}$ alkenyloxy, substituted $C_{3-6}$ alkenyloxy, (iii) di($C_{1-6}$ alkyl)amino, substituted $C_{1-6}$ alkyl-amino, di(substituted $C_{1-6}$ alkyl)amino, $C_{3-6}$ alkenyl-amino, di($C_{3-6}$ alkenyl)amino, substituted $C_{3-6}$ alkenyl-amino, di(substituted $C_{3-6}$ alkenyl)amino; and (iv) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl)piperazino, 4-N—($C_{1-6}$ alkylamino $C_{1-6}$ alkyl)piperazino, and 4-N—($C_{1-6}$ alkylamino $C_{3-6}$ alkenyl)piperazino; and (c) aryl $C_{0-11}$ alkyl wherein the aryl group is selected from phenyl, imidazolyl, furyl, thienyl.

In some embodiments, the invention provides a compound of Formula 1a, in the form of a free compound or its pharmaceutically acceptable pro-drug, metabolite, analogue, derivative, solvate or salt, for use in the methods of the invention, wherein:

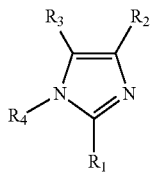

Formula 1a wherein the substituents $R_1$, $R_2$, $R_3$, and $R_4$ are defined as in A or B:

(A) $R_1$ is selected from the group consisting of:
(i) substituted $C_{1-11}$ alkyl or substituted $C_{2-11}$ alkenyl, wherein the substituents are selected from the group consisting of hydroxy and $C_{1-6}$ alkyloxy; and
(ii) mono-, di-, or tri-substituted aryl-$C_{0-11}$ alkyl wherein aryl is selected from the group consisting of phenyl, furyl, and thienyl wherein the substituents are selected from the group consisting of:
 (a) phenyl, trans-2-phenylethenyl, 2-phenylethynyl, or 2-phenylethyl, wherein the phenyl group is mono- or disubstituted wherein the substituents are selected from the group consisting of hydroxy, halo, $C_{1-4}$ alkyl and $C_{1-4}$ alkyloxy;
 (b) substituted $C_{1-6}$ alkyl, substituted $C_{2-6}$ alkyloxy, substituted $C_{2-6}$ alkylthio, or substituted $C_{2-6}$ alkoxycarbonyl, wherein the substituents are selected from the group consisting of $C_{1-4}$ alkoxy, and $C_{1-6}$ alkylthio; and
 (c) $C_{1-11}$ $CO_2R_5$, $C_{1-11}$CONH$R_5$, trans-CH=CHCO$_2R_5$, or trans-CH=CHCONH$R_5$ wherein $R_5$ is $C_{1-11}$ alkyl, phenyl $C_{1-11}$ alkyl, or $C_{1-6}$ alkoxycarbonylmethyleneoxy;

$R_2$ and $R_3$ are each independently selected from the group consisting of mono-, di, and tri-substituted phenyl wherein the substituents are independently selected from:
(i) substituted $C_{1-6}$ alkyl;
(ii) substituted $C_{1-6}$ alkyloxy, $C_{3-6}$ alkenyloxy, or substituted $C_{3-6}$ alkenyloxy;
(iii) substituted $C_{1-6}$ alkyl-amino, di(substituted $C_{1-6}$ alkyl) amino;
(iv) $C_{3-6}$ alkenyl-amino, di($C_{3-6}$ alkenyl)amino, substituted $C_{3-6}$ alkenyl-amino, or di(substituted $C_{3-6}$ alkenyl) amino; and
(v) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy-$C_{1-6}$ alkyl)piperazino, 4-N—($C_{1-6}$ alkoxy-$C_{3-4}$ alkenyl)piperazino, 4-N—($C_{1-6}$ alkylamino-$C_{1-6}$ alkyl) piperazino, or 4-N—($C_{1-6}$ alkylamino-$C_{3-6}$ alkenyl)piperazino;

wherein the substituents for (i), (ii), (iii), and (iv) are selected from the group consisting of:
(a) hydroxy, $C_{1-6}$ alkoxy, or $C_{1-6}$ alkylamino;
(b) $C_{3-6}$ alkenyloxy, or $C_{3-6}$ alkenylamino; and
(c) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl)piperazino, 4-N—($C_{1-6}$ alkylamino-$C_{1-4}$ alkyl)piperazino, or 4-N—($C_{1-6}$ alkylamino-$C_{3-6}$ alkenyl)piperazino;

or $R_2$ and $R_3$ are taken together to form an aryl group or substituted aryl, wherein the substituents are defined as above in (i)-(iv);

and $R_4$ is selected from the group consisting of:
(i) hydrogen;
(ii) substituted $C_{1-11}$ alkyl or $C_{2-11}$ alkenyl wherein the substituents are independently selected from the group consisting of hydrogen, hydroxy, $C_{1-6}$ alkyloxy, $C_{1-6}$ alkylthio, $C_{1-6}$ alkylamino, phenyl-$C_{1-6}$ alkylamino, and $C_{1-6}$ alkoxycarbonyl; and
(iii) substituted aryl $C_{0-11}$ alkyl wherein the aryl group is selected from phenyl, imidazolyl, furyl, and thienyl in which the substituents are selected from the group consisting of:
 (a) hydroxy, $C_{1-6}$ alkoxy, or $C_{1-6}$ alkylamino;
 (b) $C_{3-6}$ alkenyloxy, or $C_{3-6}$ alkenylamino; and
 (c) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl)piperazino, 4-N—($C_{1-6}$ alkylamino-$C_{1-6}$ alkyl)piperazino, or 4-N—($C_{1-6}$ alkylamino-$C_{3-6}$ alkenyl)piperazino; or (B) $R_1$ is selected from the group consisting of:
mono-, di-, and tri-substituted aryl-$C_{0-6}$ alkyl wherein aryl is selected from the group consisting of phenyl and thienyl, and the substituents are selected from the group consisting of:
(i) trans-2-substituted benzimidazolylethenyl, trans-2-substituted benzoxazolylethenyl, or trans-2-substituted benzthiazolylethenyl, in which the substituents are selected from the group consisting of hydrogen, hydroxy, halo, trihalomethyl, $C_{1-4}$ alkyl, $C_{1-4}$ alkyloxy, $C_{1-4}$ alkyloxycarbonyl, $C_{1-4}$ alkylamino, di($C_{1-4}$ alkyl) amino, $C_{3-6}$ alkenylamino, di($C_{3-6}$ alkenyl)amino, $C_{1-4}$ alkyloxy-$C_{1-4}$ alkylamino, substituted $C_{1-4}$ alkyl, substituted $C_{1-4}$ alkyloxy, substituted $C_{1-4}$ alkyloxycarbonyl, substituted $C_{1-4}$ alkylamino, di(substituted $C_{1-4}$ alkyl) amino, substituted $C_{3-6}$ alkenylamino, and di(substituted $C_{3-6}$ alkenyl)amino, wherein the substituents are selected from the group consisting of:
 (a) hydroxy, $C_{1-6}$ alkoxy, or $C_{1-6}$ alkylamino;
 (b) $C_{3-6}$ alkenyloxy, or $C_{3-6}$ alkenylamino; and
 (c) pyrrolidino, piperidino, morpholino, imidazolyl, substituted imidazolyl, piperazino, 4-N—$C_{1-6}$ alkylpiperazino, 4-N—$C_{3-4}$ alkenylpiperazino, 4-N—($C_{1-6}$ alkoxy $C_{1-6}$ alkyl)piperazino, 4-N—($C_{1-6}$ alkoxy $C_{3-6}$ alkenyl)piperazino, 4-N—($C_{1-6}$ alkylamino-$C_{1-6}$ alkyl)piperazino, or 4-N—($C_{1-6}$ alkylamino-$C_{3-6}$ alkenyl)piperazino;
(ii) trans-2-cyano ethenyl, trans-2-alkylsulfonyl ethenyl, trans-2-alkenylsulfonyl ethenyl, trans-2-substituted alkylsulfonyl ethenyl, and trans-2-substituted alkenylsulfonyl ethenyl, wherein the substituents are selected from the group consisting of:
  (a) hydroxy, $C_{1-6}$ alkoxy, or $C_{1-6}$ alkylamino;
  (b) $C_{3-6}$ alkenyloxy, or $C_{3-6}$ alkenylamino; and
  (c) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl)piperazino, 4-N—($C_{1-6}$ alkylamino-$C_{1-6}$ alkyl)piperazino, or 4-N—($C_{1-6}$ alkylamino-$C_{3-6}$ alkenyl)piperazino;

(iii) $C_{1-6}CO_2R_5$, trans-CH=CHCO$_2R_5$, $C_{1-6}$CONHR$_5$, or trans-CH=CHCONHR$_5$, wherein R$_5$ is $C_{1-6}$ alkoxy-$C_{2-6}$ alkyl, amino-$C_{2-6}$ alkyl, $C_{1-6}$ alkylamino-$C_{2-6}$ alkyl, di($C_{1-6}$ alkyl)amino-$C_{2-6}$ alkyl, $C_{1-6}$ alkylthio-$C_{2-6}$ alkyl, substituted $C_{1-6}$ alkoxy-$C_{2-6}$ alkyl, substituted $C_{1-6}$ alkylamino-$C_{2-6}$ alkyl, di(substituted $C_{1-6}$ alkyl)amino-$C_{2-6}$ alkyl, or substituted $C_{1-6}$ alkylthio-$C_{2-6}$ alkyl, in which the substituents are selected from the group consisting of pyrrolidino, piperidino morpholino, piperazino, 4-N—$C_{1-6}$ alkylpiperazino, 4-N—$C_{3-6}$ alkenylpiperazino, 4-N—($C_{1-6}$ alkoxy-$C_{1-6}$ alkyl)piperazino, 4-N—($C_{1-6}$ alkoxy-$C_{3-6}$ alkenyl)piperazino, 4-N—($C_{1-6}$ alkylamino-$C_{1-6}$ alkyl)piperazino, 4-N—($C_{1-6}$ alkylamino $C_{3-6}$ alkenyl)piperazino, imidazolyl, oxazolyl, and thiazolyl;

(iv) $C_{1-6}$CONHR$_5$, or trans-CH=CHCONR$_6$R$_7$, wherein R$_6$ and R$_7$ are independently selected from the group consisting of $C_{1-6}$ alkyl, phenyl-$C_{1-6}$ alkyl, $C_{1-6}$ alkoxycarbonylmethyleneoxy, hydroxy-$C_{2-6}$ alkyl, $C_{1-6}$ alkyloxy-$C_{2-6}$ alkyl, amino-$C_{2-6}$ alkyl, $C_{1-6}$ alkylamino-$C_{2-6}$ alkyl, di($C_{1-6}$ alkyl)amino-$C_{2-6}$ alkyl, $C_{1-6}$ alkylthio-$C_{2-6}$ alkyl, substituted $C_{1-6}$ alkoxy-$C_{2-6}$ alkyl, substituted $C_{1-6}$ alkylamino-$C_{2-6}$ alkyl, di(substituted $C_{1-6}$ alkyl)amino-$C_{2-6}$ alkyl, substituted $C_{1-6}$ alkylthio-$C_{2-6}$ alkyl, wherein the substituents are selected from the group consisting of pyrrolidino, piperidino, morpholino, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy-$C_{3-6}$ alkenyl)piperazino, 4-N—($C_{1-6}$ alkylamino-$C_{1-6}$ alkyl)piperazino, 4-N—($C_{1-6}$ alkylamino-$C_{3-6}$ alkenyl)piperazino, imidazolyl, oxazolyl, and thiazolyl;

(v) R$_7$—C(O)—$C_{1-6}$ alkyl or R$_7$—C(O)—$C_{2-6}$ alkenyl, in which R$_7$ is defined as above in [B(iv)];

(vi) HO—$C_{1-6}$ alkyl-$C_{2-6}$ alkenyl, R$_7$—O—$C_{1-6}$ alkyl-$C_{2-6}$ alkenyl, R$_7$NH—$C_{1-6}$ alkyl-$C_{2-6}$ alkenyl, R$_6$R$_7$N—$C_{1-6}$ alkyl-$C_{2-6}$ alkenyl, R$_7$NH—C(O)—O—$C_{1-6}$ alkyl-$C_{2-6}$ alkenyl, R$_6$R$_7$N—C(O)—O—$C_{1-6}$ alkyl-$C_{2-6}$ alkenyl, R$_7$O—C(O)—O—$C_{1-6}$ alkyl-$C_{2-6}$ alkenyl, or R$_7$—C(O)—O—$C_{1-6}$ alkyl-$C_{2-6}$ alkenyl, wherein R$_6$ and R$_7$ is defined as above in [B(iv)]; and (vii) R$_7$—O—$C_{0-3}$ alkyl-$C_{3-6}$ cycloalk-1-yl, R$_7$NH—$C_{0-3}$ alkyl-$C_{3-6}$ cycloalk-1-yl, R$_6$R$_7$N—$C_{0-3}$ alkyl-$C_{3-6}$ cycloalk-1-yl, R$_7$NH—C(O)—O—$C_{0-3}$ $C_{3-6}$ cycloalk-1-yl, R$_6$R$_7$N—C(O)—O—$C_{0-3}$ alkyl-$C_{3-6}$ cycloalk-1-yl, R$_7$O—C(O)—O—$C_{0-3}$ alkyl-$C_{3-6}$ cycloalk-1-yl, R$_7$—C(O)—O—$C_{0-3}$ alkyl-$C_{3-6}$ cycloalk-1-yl, R$_7$O—C(O)—Co-3 alkyl-$C_{3-6}$ cycloalk-1-yl, wherein R$_7$ and R$_6$ are defined as above in [B(iv)];

R$_2$ and R$_3$ are each independently selected from the group consisting of:

(viii) hydrogen, halo, trihalomethyl, $C_{1-6}$ alkyl, substituted $C_{1-6}$ alkyl, $C_{2-6}$ alkenyl, substituted $C_{2-6}$ alkenyl, $C_{1-6}$ alkyloxy, substituted $C_{1-6}$ alkyloxy, $C_{3-6}$ alkenyloxy, substituted $C_{3-6}$ alkenyloxy, $C_{1-6}$ alkylamino, substituted $C_{1-6}$ alkylamino, $C_{3-6}$ alkenylamino, or substituted $C_{3-6}$ alkenylamino; and (ix) mono-, di-, or tri-substituted phenyl wherein the substituents are independently selected from the group consisting of:
  (a) halo, trifluoromethyl, or substituted $C_{1-6}$ alkyl;
  (b) $C_{1-6}$ alkyloxy, substituted $C_{1-6}$ alkyloxy, $C_{3-6}$ alkenyloxy, substituted $C_{3-6}$ alkenyloxy;
  (c) $C_{1-6}$ alkyl-amino, di($C_{1-6}$ alkyl)amino, substituted $C_{1-6}$ alkyl-amino, di(substituted $C_{1-6}$ alkyl)amino, $C_{3-6}$ alkenyl-amino, di($C_{3-6}$ alkenyl)amino, substituted $C_{3-6}$ alkenyl-amino, or di(substituted $C_{3-6}$ alkenyl)amino; and
  (d) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-4}$ alkoxy $C_{1-6}$ alkyl)piperazino, 4-N—($C_{1-4}$ alkoxy $C_{3-6}$ alkenyl) piperazino, 4-N—($C_{1-6}$ alkylamino $C_{1-6}$ alkyl)piperazino, or 4-N—($C_{1-6}$ alkylamino $C_{3-6}$ alkenyl)piperazino;

wherein the substituents for (a), (b), (c), and (d) are selected from the group consisting of:
  (1) hydrogen, hydroxy, halo, or trifluoromethyl;
  (2) $C_{1-4}$ alkylalkoxy, $C_{1-6}$ alkylamino, or $C_{1-6}$ alkylthio;
  (3) $C_{3-6}$ alkenyloxy, $C_{3-6}$ alkenylamino, or $C_{3-4}$ alkenylthio; and
  (4) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-4}$ alkoxy $C_{1-6}$ alkyl)piperazino, 4-N—($C_{1-6}$ alkoxy $C_{3-6}$ alkenyl) piperazino, 4-N—($C_{1-6}$ alkylamino $C_{1-6}$ alkyl)piperazino, or 4-N—($C_{1-6}$ alkylamino $C_{3-6}$ alkenyl)piperazino;

with the proviso that a) at least one of R$_2$ and R$_3$ is selected from [B (ix)] and wherein the substituents are selected from [B (ix) (b)-(d)] above; or b) R$_2$ and R$_3$ are taken together to form an optionally substituted aryl group, wherein the substituents are defined as above in [B (ix) (a)-(d)];

and R$_4$ is selected from the group consisting of:
(i) hydrogen;
(ii) substituted $C_{1-11}$ alkyl or $C_{2-11}$ alkenyl wherein the substituents are independently selected from the group consisting of:
  (a) hydrogen, hydroxy, $C_{1-6}$ alkyloxy, $C_{1-6}$ alkylthio, $C_{1-6}$ alkylamino, phenyl-$C_{1-4}$ alkylamino, or $C_{1-6}$ alkoxycarbonyl;
  (b) substituted $C_{1-6}$ alkyloxy, $C_{3-6}$ alkenyloxy, or substituted $C_{3-6}$ alkenyloxy;
  (c) di($C_{1-6}$ alkyl)amino, substituted $C_{1-6}$ alkyl-amino, di(substituted $C_{1-6}$ alkyl)amino, $C_{3-6}$ alkenyl-amino, di($C_{3-4}$ alkenyl)amino, substituted $C_{3-6}$ alkenyl-amino, or di(substituted $C_{3-4}$ alkenyl)amino; and
  (d) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl)piperazino, 4-N—($C_{1-6}$ alkylamino $C_{1-6}$ alkyl)piperazino, or 4-N—($C_{1-6}$ alkylamino $C_{3-6}$ alkenyl)piperazino; and (iii) aryl $C_{0-11}$ alkyl wherein the aryl group is selected from phenyl, imidazolyl, furyl, or thienyl.

In some embodiments of the invention, the compound of Formula 1a is a compound wherein R$_1$ is selected from the group consisting of mono-, di-, and tri-substituted aryl-$C_{0-6}$ alkyl wherein aryl is selected from the group consisting of phenyl and thienyl, and the substituents are selected from the group consisting of:

(a) $C_{1-6}CO_2R_5$, trans-CH=CHCO$_2$R$_5$, $C_{1-6}$CONHR$_5$, or trans-CH=CHCONHR$_5$;

(b) $C_{1-6}$CONR$_6$R$_7$, or trans-CH=CHCONR$_6$R$_7$;

(c) $R_7$C(O)C$_{1-6}$ alkyl or $R_7$C(O)C$_{2-6}$ alkenyl; and (d) HO—C$_{1-6}$ alkyl-C$_{2-6}$ alkenyl, R$_7$—O—C$_{1-6}$ alkyl-C$_u$ alkenyl, R$_7$NH—C$_{1-6}$ alkyl-C$_{2-6}$ alkenyl, R$_6$R$_7$N—C$_{1-6}$ alkyl-C$_{2-6}$ alkenyl, R$_7$NH—C(O)—O—C$_{1-6}$ alkyl-C$_{2-6}$ alkenyl, R$_6$R$_7$N—C(O)—O—C$_{1-6}$ alkyl-C$_u$ alkenyl, R$_7$O—C(O)—O—C$_{1-6}$ alkyl-C$_{2-6}$ alkenyl, or R$_7$—C(O)—O—C$_{1-6}$ alkyl-C$_{2-4}$ alkenyl.

In other embodiments, the compound of Formula 1a is a compound wherein R$_1$ is selected from the group consisting of mono-, di-, and tri-substituted aryl-C$_{0-6}$ alkyl wherein aryl is selected from the group consisting of phenyl and thienyl, and the substituents are selected from the group consisting of:

(a) $C_{1-6}CO_2R_5$, trans-CH=CHCO$_2$R$_5$, $C_{1-6}$CONHR$_5$, or trans-CH=CHCONHR$_5$;

(b) $C_{1-6}$CONR$_6$R$_7$, or trans-CH=CHCONR$_6$R$_7$;

(c) $R_7$C(O)C$_{1-6}$ alkyl or $R_7$C(O)C$_{2-6}$ alkenyl; and (d) HO—C$_{1-6}$ alkyl-C$_{2-6}$ alkenyl, R$_7$—O—C$_{1-6}$ alkyl-C$_{2-6}$ alkenyl, R$_7$NH—C$_{1-6}$ alkyl-C$_{2-6}$ alkenyl, R$_6$R$_7$N—C$_{1-6}$ alkyl-C$_{2-6}$ alkenyl, R$_7$NH—C(O)—O—C$_{1-6}$ alkyl-C$_{2-6}$ alkenyl, R$_6$R$_7$N—C(O)—O—C$_{1-6}$ alkyl-C$_{2-6}$ alkenyl, R$_7$O—C(O)—O—C$_{1-6}$ alkyl-C$_{2-6}$ alkenyl, or R$_7$—C(O)—O—C$_{1-6}$ alkyl-C$_{2-6}$ alkenyl.

In various embodiments of the invention, the compound of Formula 1a is a compound wherein R$_1$ is selected from the group consisting of mono-, di-, and tri-substituted aryl-C$_{0-6}$ alkyl wherein aryl is selected from the group consisting of phenyl and thienyl, and the substituents are HO—C$_{1-6}$ alkyl-C$_{2-6}$ alkenyl, R$_7$—O—C$_{1-6}$ alkyl-C$_{2-6}$ alkenyl, R$_7$NH—C$_{1-6}$ alkyl-C$_{2-6}$ alkenyl, R$_6$R$_7$N—C$_{1-6}$ alkyl-C$_{2-6}$ alkenyl, R$_7$NH—C(O)—O—C$_{1-6}$ alkyl-C$_{2-6}$ alkenyl, R$_6$R$_7$N—C(O)—O—C$_{1-6}$ alkyl-C$_{2-6}$ alkenyl, R$_7$O—C(O)—O—C$_{1-6}$ alkyl-C$_{2-6}$ alkenyl, or R$_7$—C(O)—O—C$_{1-6}$ alkyl-C$_{2-6}$ alkenyl.

In other embodiments, R$_1$ is selected from the group consisting of mono-, di-, and tri-substituted aryl-C$_{0-6}$ alkyl wherein the aryl-C$_{0-6}$ alkyl is phenyl-C$_{0-6}$ alkyl. In some embodiments, R$_1$ is selected from the group consisting of mono-, di-, and tri-substituted aryl-C$_{0-6}$ alkyl wherein the aryl-C$_{0-6}$ alkyl is aryl-C$_0$alkyl, which is aryl with no alkyl group attached directly to aryl.

In various embodiments, R$_2$ and R$_3$ are each independently selected from the group consisting of: mono-, di-, and tri-substituted phenyl wherein the substituents are independently selected from the group consisting of:

(i) $C_{1-6}$ alkyloxy, substituted $C_{1-6}$ alkyloxy, $C_{3-6}$ alkenyloxy, or substituted $C_{3-6}$ alkenyloxy;

(ii) $C_{1-6}$ alkyl-amino, di($C_{1-6}$ alkyl)amino, substituted $C_{1-6}$ alkyl-amino, di(substituted $C_{1-6}$ alkyl)amino, $C_{3-6}$ alkenyl-amino, di($C_{3-6}$ alkenyl)amino, substituted $C_{3-6}$ alkenyl-amino, or di(substituted $C_{3-6}$ alkenyl)amino, and (iii) pyrrolidino, piperidino, morpholino, imidazolyl, substituted imidazolyl, piperazino, 4-N—C$_{1-6}$ alkylpiperazino, 4-N—C$_{3-6}$ alkenylpiperazino, 4-N—(C$_{1-6}$ alkoxy C$_{1-6}$ alkyl)piperazino, 4-N—(C$_{1-6}$ alkoxy C$_{3-6}$ alkenyl)piperazino, 4-N—(C$_{1-6}$ alkylamino C$_{1-6}$ alkyl)piperazino, or 4-N—(C$_{1-6}$ alkylamino C$_{3-6}$ alkenyl)piperazino.

In some embodiments, R$_2$ and R$_3$ are each independently selected from the group consisting of: mono-, di-, and tri-substituted phenyl wherein the substituents are independently selected from the group consisting of C$_{1-6}$ alkyl-amino, di(C$_{1-6}$ alkyl)amino, substituted C$_{1-6}$ alkyl-amino, di(substituted C$_{1-6}$ alkyl)amino, C$_{3-6}$ alkenyl-amino, di(C$_{3-6}$ alkenyl)amino, substituted C$_{3-6}$ alkenyl-amino, and di(substituted C$_{3-6}$ alkenyl)amino.

In some embodiments, R$_4$ is hydrogen.

In some embodiments, the compound of Formula 1a is a compound of Formula 1b:

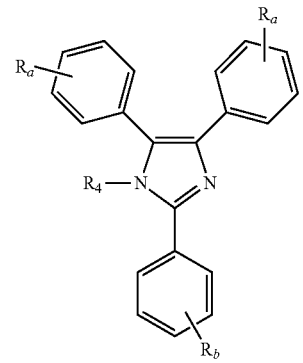

Formula 1b wherein each instance of R$_a$ is independently C$_{1-6}$ alkyl-amino, di(C$_{1-6}$ alkyl)amino, substituted C$_{1-6}$ alkyl-amino, di(substituted alkyl)amino, C$_{3-6}$ alkenyl-amino, di(C$_{3-6}$ alkenyl)amino, substituted C$_{3-6}$ alkenyl-amino, or di(substituted C$_{3-6}$ alkenyl)amino; and R$_b$ is HO—C$_{1-6}$ alkyl-C$_{2-6}$ alkenyl, R$_7$—O—C$_{1-6}$ alkyl-C$_{2-6}$ alkenyl, R$_7$NH—C$_{1-6}$ alkyl-C$_{2-6}$ alkenyl, R$_6$R$_7$N—C$_{1-6}$ alkyl-C$_{2-6}$ alkenyl, R$_7$NH—C(O)—O—C$_{1-6}$ alkyl-C$_{2-6}$ alkenyl, R$_6$R$_7$N—C(O)—O—C$_{1-6}$ alkyl-C$_{2-6}$ alkenyl, R$_7$O—C(O)—O—C$_{1-6}$ alkyl-C$_{2-6}$ alkenyl, or R$_7$—C(O)—O—C$_{1-6}$ alkyl-C$_{2-6}$ alkenyl.

In preferred embodiments, the compound is of Formula 2:

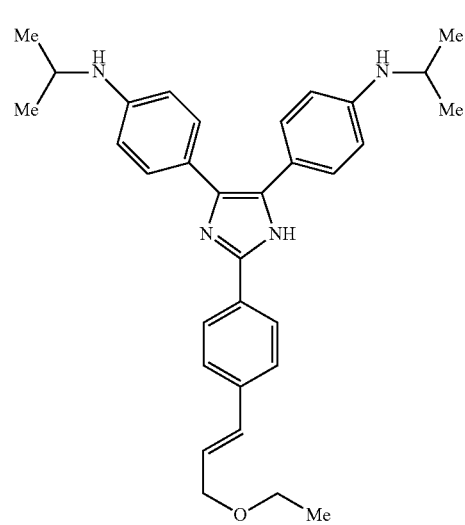

Formula 2 in the form of a free compound or as its pharmaceutically-acceptable pro-drug, metabolite, analogue, derivative, solvate or salt.

In some aspects of the present invention, the compound of Formula 1 or 1a (such as Formula 1b or 2) is adminstered to a subject suffering from a lysosomal storage disease. The lysosomal storage disease may be characterized by a defect in glycosphingolipid synthesis. In some embodiments, the defect is in neutral glycosphingolipid synthesis. In other embodiments, the disease is characterized by a defect in ceramide synthesis. The disease may be Gaucher's disease or Fabry's disease. In some embodiments, the lysosomal storage disease may be characterized by a defect in ganglioside synthesis in the subject, wherein the ganglioside is a GM1 or GM2 ganglioside. The disease may be Tay Sach's disease, Sandhoff's disease, or cystic fibrosis.

In another aspect of the present invention, a method for treating a lipid storage disease in a subject comprising administering to the subject an effective amount of: a first compound of Formula 1 or 1a (such as Formula 1b or 2) and a second compound effective to treat the lipid storage disease, is provided. In some embodiments, the second compound is a glucosylceramide synthase inhibitor. In preferred embodiments, the glucosylceramide synthase inhibitor is miglustat. In other embodiments, the second compound is an enzyme administered as enzyme replacement therapy or a pharmacological chaperone which binds to the enzyme and promotes trafficking of the enzyme from the endoplasmic reticulum to the lysosome.

In yet another aspect, the present invention provides a method for treating a subject having a condition associated with verotoxin, cholera toxin, or uropathic *E. coli* comprising administering an effective amount of a composition of a compound of Formula 1 or 1a (such as Formula 1b or 2) to a subject in need thereof.

The present invention further provides compositions comprising a glucosylceramide synthase inhibitor and compound of Formula 1 or 1a (such as Formula 1b or 2). In some embodiments, the glucosylceramide synthase inhibitor is miglustat.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
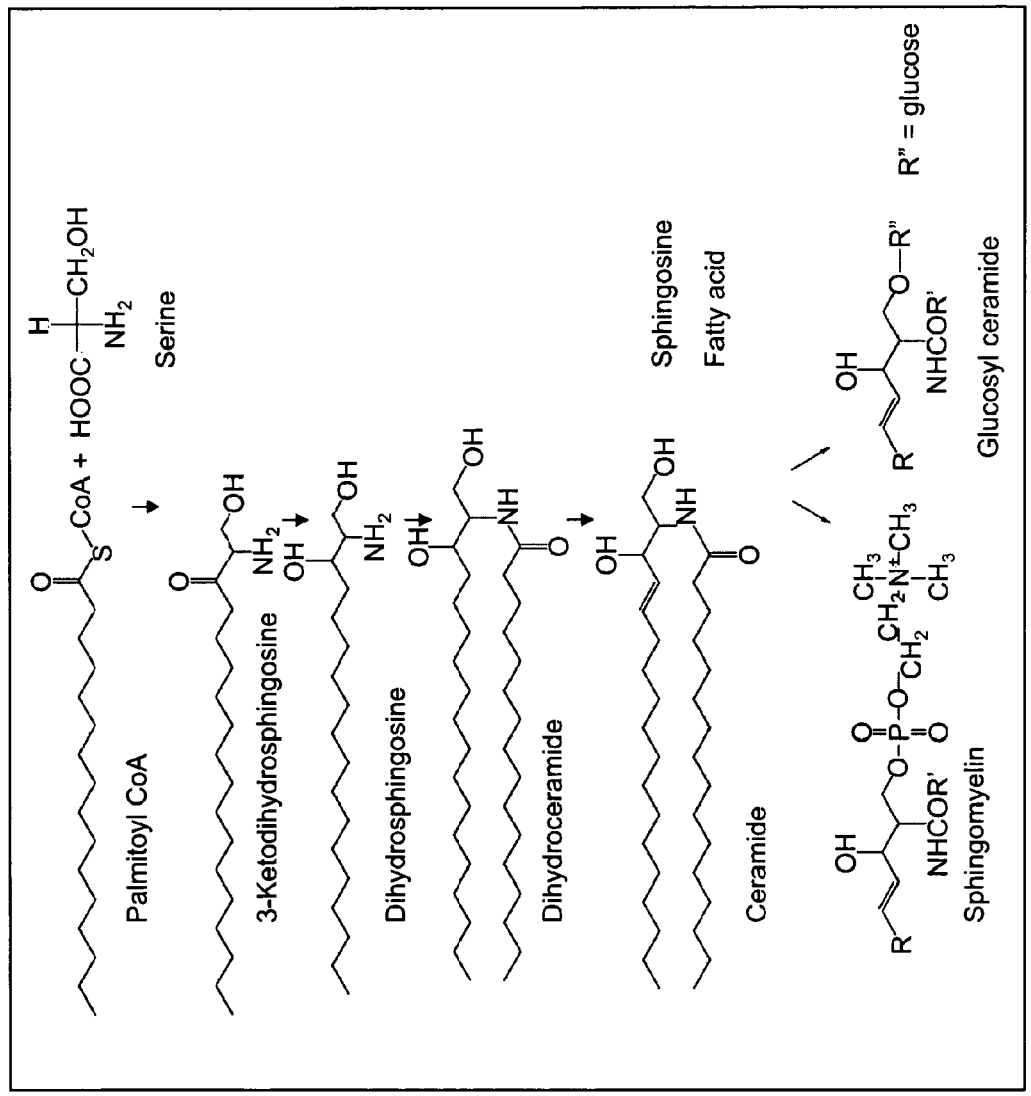
FIG. 1 depicts the glucosylceramide pathway.

The present invention describes methods of modulating GSL levels using a class of substituted imidazole derivatives or compounds. The compounds are useful in modulating GSL accumulation, for example complex GSLs, such as neutral GSLs. In another aspect, the compounds are useful in modulating a subset of GSLs, such as neutral GSLs (for example, GlcCer, LacCer, Gb3, Gb4) or acidic GSLs, such as gangliosides. Such compounds are useful for treating conditions involving abnormal glycolipid synthesis or metabolism, for example resulting in accumulation of a GSL.

I. Compounds Useful for Modulating GSL Levels

The class of imidazole derivatives or compounds is as depicted in Formula 1:

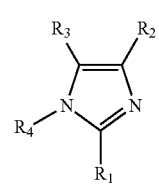

Formula 1 in the form of a free compound or its pharmaceutically acceptable pro-drug, metabolite, analogue, derivative, solvate or salt wherein the substituents $R_1$, $R_2$, $R_3$, and $R_4$ are defined as described in (a) and (b) below:

(a) when $R_1$ is selected from the group consisting of:
  (i) substituted $C_{1-11}$ alkyl or substituted $C_{2-11}$ alkenyl, wherein the substituents are selected from the group consisting of hydroxy, $C_{1-6}$ alkyloxy; or
  (ii) mono-, di-, and tri-substituted aryl-$C_{0-11}$ alkyl wherein aryl is selected from the group consisting of phenyl, furyl, thienyl wherein the substituents are selected from the group consisting of:
   (a) phenyl, trans-2-phenylethenyl, 2-phenylethynyl, 2-phenylethyl, wherein the said phenyl group is mono- or disubstituted with a member selected from the group consisting of hydroxy, halo, $C_{1-4}$ alkyl and $C_{1-4}$ alkyloxy,
   (b) substituted $C_{1-6}$ alkyl, substituted $C_{2-6}$ alkyloxy, substituted $C_{2-6}$ alkylthio, substituted $C_{2-6}$ alkoxycarbonyl, wherein the substituents are selected from the group consisting of $C_{1-6}$ alkoxy, and $C_{1-6}$ alkylthio; and
   (c) $C_{1-11}$ $CO_2R_5$, $C_{1-11}$ $CONHR_5$, trans-CH=CHCO$_2R_5$, or trans-CH=CHCONHR$_5$ wherein R$_5$ is $C_{1-11}$ alkyl, or phenyl $C_{1-11}$ alkyl, $C_{1-6}$ alkoxycarbonylmethyleneoxy;
then $R_2$ and $R_3$ are each independently selected from the group consisting of mono-, di, and tri-substituted phenyl wherein the substituents are independently selected from:
  (i) substituted $C_{1-6}$ alkyl,
  (ii) substituted $C_{1-6}$ alkyloxy, $C_{3-6}$ alkenyloxy, substituted $C_{3-6}$ alkenyloxy,
  (iii) substituted $C_{1-6}$ alkyl-amino, disubstituted $C_{1-6}$ alkyl) amino,
  (iv) $C_{3-6}$ alkenyl-amino, di($C_{3-6}$ alkenyl)amino, substituted $C_{3-6}$ alkenyl-amino, di(substituted $C_{3-6}$ alkenyl)amino,
  (v) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl) piperazino, 4-N—($C_{1-6}$ alkylamino $C_{1-6}$ alkyl)piperazino, 4-N—($C_{1-6}$, alkylamino $C_{3-6}$ alkenyl)piperazino, wherein the substituents are selected from the group consisting of:
   (a) hydroxy, $C_{1-6}$ alkylalkoxy, $C_{1-6}$ alkylamino
   (b) $C_{3-6}$ alkenyloxy, $C_{3-6}$ alkenylamino, or
   (c) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl)piperazino, 4-N—($C_{1-6}$ alkylamino alkyl)piperazino, 4-N—($C_{1-6}$ alkylamino $C_{3-6}$ alkenyl)piperazino, or $R_2$ and $R_3$ taken together forming an aryl group or substituted aryl, wherein the substituents are defined as above in (i)-(v);

and $R_4$ is selected from the group consisting of:
(i) hydrogen;
(ii) substituted $C_{1-11}$ alkyl or $C_{2-11}$ alkenyl wherein the substituents are independently selected from the group consisting of hydrogen, hydroxy, $C_{1-6}$ alkyloxy, $C_{1-6}$alkylthio, $C_{1-6}$ alkylamino, phenyl-$C_{1-6}$ alkylamino, $C_{1-6}$ alkoxycarbonyl; or
(iii) substituted aryl $C_{0-11}$ alkyl wherein the aryl group is selected from phenyl, imidazolyl, furyl, thienyl in which the substituents are selected from A(a-c); or (b) when $R_1$ is selected from the group consisting of:
Mono-, di-, and tri-substituted aryl-$C_{2-6}$ alkyl wherein aryl is selected from the group consisting of phenyl, thienyl, and the substituents are selected from the group consisting of:
(a) trans-2-substituted benzimidazolylethenyl, trans-2-substituted benzoxazolylethenyl, trans-2-substituted benzthiazolylethenyl, in which the substituents are selected from the group consisting of hydrogen, hydroxy, halo, trihalomethyl, $C_{1-4}$ alkyl and $C_{1-4}$ alkyloxy, $C_{1-4}$ alkyloxycarbonyl, $C_{1-4}$ alkylamino, di($C_{1-4}$ alkyl)amino, $C_{3-6}$ alkenylamino, di($C_{3-6}$ alkenyl)amino, $C_{1-4}$ alkyloxy-$C_{1-4}$ alkylamino, substituted $C_{1-4}$ alkyl and $C_{1-4}$ alkyloxy, substituted $C_{1-4}$ alkyloxycarbonyl, substituted $C_{1-4}$ alkylamino, di(substituted $C_{1-4}$ alkyl) amino, substituted $C_{3-4}$ alkenylamino, di(substituted $C_{3-6}$ alkenyl)amino, wherein the substituents are as defined above,
(b) trans-2-cyano ethenyl, trans-2-alkylsulfonyl ethenyl, trans-2-alkenylsulfonyl ethenyl, trans-2-substituted alkylsulfonyl ethenyl, trans-2-substituted alkenylsulfonyl ethenyl, in which the substituents are defined above,
(c) $C_{1-6}$ $CO_2R_5$, trans-CH=CHCO$_2R_5$, $C_{1-6}$CONHR$_5$, or trans-CH=CHCONHR$_5$, wherein $R_5$ is $C_{1-6}$ alkoxy $C_{2-6}$ alkyl, amino $C_{2-6}$ alkyl, $C_{1-6}$ alkylamino $C_{2-6}$ alkyl, di($C_{1-6}$ alkyl)amino $C_{2-6}$ alkyl, $C_{1-6}$ alkylthio $C_{2-6}$ alkyl, substituted $C_{1-6}$ alkoxy $C_{2-6}$ alkyl, substituted $C_{1-6}$ alkylamino $C_{2-6}$ alkyl, di(substituted $C_{1-6}$ alkyl)amino $C_{2-6}$ alkyl, substituted $C_{1-6}$ alkylthio $C_{2-6}$ alkyl, in which the substituents are selected from the group consisting of pyrrolidino, piperidino morpholino, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl)piperazino, 4-N—($C_{1-6}$ alkylamino $C_{1-6}$ alkyl)piperazino, 4-N—($C_{1-6}$ alkylamino $C_{3-6}$ alkenyl)piperazino, imidazolyl, oxazolyl, thiazolyl,
(d) $C_{1-6}$CONR$_6$R$_7$, or trans-CH=CHCONR$_6$R$_7$, wherein $R_6$ and $R_7$ are independently selected from the group consisting of $C_{1-6}$ alkyl, phenyl $C_{1-6}$ alkyl, $C_{1-6}$ alkoxycarbonylmethyleneoxy, hydroxy $C_{2-6}$ alkyl, $C_{1-6}$ alkyloxy $C_{2-6}$ alkyl, amino $C_{2-6}$ alkyl, $C_{1-6}$ alkylamino $C_{2-6}$ alkyl, di($C_{1-6}$ alkyl)amino $C_{2-6}$ alkyl, $C_{1-6}$ alkylthio $C_{2-6}$ alkyl, substituted $C_{1-6}$ alkoxy $C_{2-6}$ alkyl, substituted $C_{1-6}$ alkylamino $C_{2-6}$ alkyl, di(substituted $C_{1-6}$ alkyl)amino $C_{2-6}$ alkyl, substituted $C_{1-6}$ alkylthio $C_{2-6}$ alkyl, wherein the substituents are selected from the group consisting of pyrrolidino, piperidino, morpholino, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl)piperazino, 4-N—($C_{1-6}$ alkylamino $C_{1-6}$ alkyl)piperazino, 4-N—($C_{1-6}$ alkylamino $C_{3-6}$ alkenyl)piperazino, imidazolyl, oxazolyl, thiazolyl,
(e) $R_7$C(O)$C_{1-6}$ alkyl, $R_7$C(O)$C_{2-6}$ alkenyl, in which $R_7$ is defined as above [2(d)],
(f) HO—$C_{1-6}$ alkyl-$C_{2-6}$ alkenyl, $R_7$—O—$C_{1-6}$ alkyl-$C_{2-6}$ alkenyl, $R_7$NH—$C_{1-6}$ alkyl-$C_{2-6}$ alkenyl, $R_6R_7$N—$C_{1-6}$ alkyl-$C_{2-6}$ alkenyl, $R_7$NH—C(O)—O—$C_{1-6}$ alkyl-$C_{2-6}$ alkenyl, $R_6R_7$N—C(O)—O—$C_{1-6}$ alkyl-$C_{2-6}$ alkenyl, $R_7$O—C(O)—O—$C_{1-6}$alkyl-$C_{2-6}$ alkenyl, $R_7$—C(O)—O—$C_{1-6}$ alkyl-$C_{2-6}$ alkenyl, wherein $R_6$ and $R_7$ is defined as above [2(d)],
(g) $R_7$—O—$C_{0-3}$ alkyl-$C_{3-6}$ cycloalkan-1-yl, $R_7$NH—$C_{0-3}$ alkyl-$C_{3-6}$ cycloalkan-1-yl, $R_6R_7$N—$C_{0-3}$ alkyl-$C_{3-6}$ cycloalkan-1-yl, $R_7$NH—C(O)—O—$C_{0-3}$ $C_{3-6}$ cycloalkan-1-yl, $R_6R_7$N—C(O)—O—$C_{0-3}$ alkyl-$C_{3-6}$ cycloalkan-1-yl, $R_7$O—C(O)—O—$C_{0-3}$ alkyl-$C_{3-6}$cycloalkan-1-yl, $R_7$—C(O)—O—$C_{0-3}$ alkyl-$C_{3-6}$ cycloalkan-1-yl, $R_7$O—C(O)—Co-3 alkyl-$C_{3-6}$ cycloalkan-1-yl, wherein $R_7$ and is defined as above [B(d)];
then $R_2$ and $R_3$ are each independently selected from the group consisting of:
(1) hydrogen, halo, trihalomethyl, $C_{1-6}$ alkyl, substituted $C_{1-6}$ alkyl, $C_{2-6}$ alkenyl, substituted $C_{1-6}$ alkenyl, $C_{1-6}$ alkyloxy, substituted $C_{1-6}$ alkyloxy, $C_{3-6}$ alkenyloxy, substituted $C_{3-6}$ alkenyloxy, $C_{1-6}$ alkylamino, substituted $C_{1-6}$ alkylamino, $C_{3-6}$ alkenylamino, substituted $C_{3-6}$ alkenylamino,
(2) mono-, di-, and tri-substituted phenyl wherein the substituents are independently selected from:
(i) halo, trifluoromethyl, substituted $C_{1-6}$ alkyl,
(ii) $C_{1-6}$ alkyloxy, substituted $C_{1-6}$ alkyloxy, $C_{3-6}$ alkenyloxy, substituted $C_{3-6}$ alkenyloxy,
(iii) $C_{1-6}$ alkyl-amino, di($C_{1-6}$ alkyl)amino, substituted $C_{1-6}$ alkyl-amino, di(substituted $C_{1-6}$ alkyl)amino, $C_{3-6}$ alkenyl-amino, di($C_{3-6}$ alkenyl)amino, substituted $C_{3-6}$ alkenyl-amino, di(substituted $C_{3-6}$ alkenyl)amino, or
(iv) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl) piperazino, 4-N—($C_{1-6}$ alkylamino $C_{1-6}$ alkyl)piperazino, 4-N—($C_{1-6}$ alkylamino $C_{3-6}$ alkenyl)piperazino,
wherein the substituents are selected from the group consisting of:
(a) hydrogen, hydroxy, halo, trifluoromethyl,
(b) $C_{1-6}$ alkylalkoxy, $C_{1-6}$ alkylamino, $C_{1-6}$ alkylthio,
(c) $C_{3-6}$ alkenyloxy, $C_{3-6}$ alkenylamino, $C_{3-6}$ alkenylthio, or
(d) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl) piperazino, 4-N—($C_{1-6}$ alkylamino $C_{1-6}$ alkyl)piperazino, 4-N—($C_{1-6}$ alkylamino $C_{3-6}$ alkenyl)piperazino;
with the proviso that at least one of $R_2$ and $R_3$ group be selected from [B (2)] and the phenyl and the substituents be selected from (ii)-(v) above; or $R_2$ and $R_3$ taken together forming an aryl group such as phenyl, pyridyl, in which the aryl may be optionally substituted, wherein the substituents are defined as above in (i)-(iv);

and $R_4$ is selected from the group consisting of:
(a) hydrogen;
(b) substituted $C_{1-11}$ alkyl or $C_{2-11}$ alkenyl wherein the substituents are independently selected from the group consisting of:
(i) hydrogen, hydroxy, $C_{1-6}$ alkyloxy, $C_{1-6}$alkylthio, $C_{1-6}$ alkylamino, phenyl-$C_{1-6}$ alkylamino, $C_{1-6}$ alkoxycarbonyl;
(ii) substituted $C_{1-6}$ alkyloxy, $C_{3-6}$ alkenyloxy, substituted $C_{3-6}$ alkenyloxy, (iii) di($C_{1-6}$ alkyl)amino, substituted $C_{1-6}$ alkyl-amino, di(substituted $C_{1-6}$ alkyl)amino, $C_{3-6}$ alkenyl-amino, di($C_{3-6}$ alkenyl)amino, substituted $C_{3-6}$ alkenyl-amino, di(substituted $C_{3-6}$ alkenyl)amino; and (iv) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl)piperazino, 4-N—($C_{1-6}$ alkylamino $C_{1-6}$ alkyl)piperazino, and 4-N—($C_{1-6}$ alkylamino $C_{3-6}$ alkenyl)piperazino; and (d) aryl $C_{0-11}$ alkyl wherein the aryl group is selected from phenyl, imidazolyl, furyl, thienyl.

In some embodiments, the invention provides a compound of Formula 1a, in the form of a free compound or its pharmaceutically acceptable pro-drug, metabolite, analogue, derivative, solvate or salt, for use in the methods of the invention, wherein:

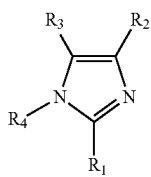

Formula 1a wherein the substituents $R_1$, $R_2$, $R_3$, and $R_4$ are defined as in A or B:

(B) $R_1$ is selected from the group consisting of:
(i) substituted $C_{1-11}$ alkyl or substituted $C_{2-11}$ alkenyl, wherein the substituents are selected from the group consisting of hydroxy and $C_{1-6}$ alkyloxy; and
(ii) mono-, di-, or tri-substituted aryl-$C_{0-11}$ alkyl wherein aryl is selected from the group consisting of phenyl, furyl, and thienyl wherein the substituents are selected from the group consisting of:
  (a) phenyl, trans-2-phenylethenyl, 2-phenylethynyl, or 2-phenylethyl, wherein the phenyl group is mono- or disubstituted wherein the substituents are selected from the group consisting of hydroxy, halo, $C_{1-4}$ alkyl and $C_{1-4}$ alkyloxy;
  (b) substituted $C_{1-6}$ alkyl, substituted $C_{2-6}$ alkyloxy, substituted $C_{2-6}$ alkylthio, or substituted $C_{2-6}$ alkoxycarbonyl, wherein the substituents are selected from the group consisting of $C_{1-6}$ alkoxy, and $C_{1-6}$ alkylthio; and
  (c) $C_{1-11}$ $CO_2R_5$, $C_{1-11}CONHR_5$, trans-CH=CHCO$_2R_5$, or trans-CH=CHCONHR$_5$ wherein $R_5$ is $C_{1-11}$ alkyl, phenyl $C_{1-11}$ alkyl, or $C_{1-6}$ alkoxycarbonylmethyleneoxy;

$R_2$ and $R_3$ are each independently selected from the group consisting of mono-, di, and tri-substituted phenyl wherein the substituents are independently selected from:
(i) substituted $C_{1-6}$ alkyl;
(ii) substituted $C_{1-6}$ alkyloxy, $C_{3-6}$ alkenyloxy, or substituted $C_{3-6}$ alkenyloxy;
(iii) substituted $C_{1-6}$ alkyl-amino, di(substituted $C_{1-6}$ alkyl) amino;
(iv) $C_{3-6}$ alkenyl-amino, di($C_{3-6}$ alkenyl)amino, substituted $C_{3-6}$ alkenyl-amino, or di(substituted $C_{3-6}$ alkenyl) amino; and
(v) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy-$C_{1-6}$ alkyl)piperazino, 4-N—($C_{1-6}$ alkoxy-$C_{3-6}$ alkenyl)piperazino, 4-N—($C_{1-6}$ alkylamino-$C_{1-6}$ alkyl)piperazino, or 4-N—($C_{1-6}$ alkylamino-$C_{3-6}$ alkenyl)piperazino;

wherein the substituents for (i), (ii), (iii), and (iv) are selected from the group consisting of:
(a) hydroxy, $C_{1-6}$ alkoxy, or $C_{1-6}$ alkylamino;
(b) $C_{3-6}$ alkenyloxy, or $C_{3-6}$ alkenylamino; and
(c) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl) piperazino, 4-N—($C_{1-6}$ alkylamino-$C_{1-6}$ alkyl)piperazino, or 4-N—($C_{1-6}$ alkylamino-$C_{3-6}$ alkenyl)piperazino;

or $R_2$ and $R_3$ are taken together to form an aryl group or substituted aryl, wherein the substituents are defined as above in (i)-(iv);

and $R_4$ is selected from the group consisting of:
(i) hydrogen;
(ii) substituted $C_{1-11}$ alkyl or $C_{2-11}$ alkenyl wherein the substituents are independently selected from the group consisting of hydrogen, hydroxy, $C_{1-6}$ alkyloxy, $C_{1-6}$alkylthio, $C_{1-6}$ alkylamino, phenyl-$C_{1-6}$ alkylamino, and $C_{1-6}$ alkoxycarbonyl; and
(iii) substituted aryl $C_{0-11}$ alkyl wherein the aryl group is selected from phenyl, imidazolyl, furyl, and thienyl in which the substituents are selected from the group consisting of:
(a) hydroxy, $C_{1-6}$ alkoxy, or $C_{1-6}$ alkylamino;
(b) $C_{3-6}$ alkenyloxy, or $C_{3-6}$ alkenylamino; and
(c) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl)piperazino, 4-N—($C_{1-6}$ alkylamino-$C_{1-6}$ alkyl)piperazino, or 4-N—($C_{1-6}$ alkylamino-$C_{3-6}$ alkenyl)piperazino; or (B) $R_1$ is selected from the group consisting of:
mono-, di-, and tri-substituted aryl-$C_{0-6}$ alkyl wherein aryl is selected from the group consisting of phenyl and thienyl, and the substituents are selected from the group consisting of:
(i) trans-2-substituted benzimidazolylethenyl, trans-2-substituted benzoxazolylethenyl, or trans-2-substituted benzthiazolylethenyl, in which the substituents are selected from the group consisting of hydrogen, hydroxy, halo, trihalomethyl, $C_{1-4}$ alkyl, $C_{1-4}$ alkyloxy, $C_{1-4}$ alkyloxycarbonyl, $C_{1-4}$ alkylamino, di($C_{1-4}$ alkyl) amino, $C_{3-6}$ alkenylamino, di($C_{3-6}$ alkenyl)amino, $C_{1-4}$ alkyloxy-$C_{1-4}$ alkylamino, substituted $C_{1-4}$ alkyl, substituted $C_{1-4}$ alkyloxy, substituted $C_{1-4}$ alkyloxycarbonyl, substituted $C_{1-4}$ alkylamino, di(substituted $C_{1-4}$ alkyl) amino, substituted $C_{3-6}$ alkenylamino, and di(substituted $C_{3-6}$ alkenyl)amino, wherein the substituents are selected from the group consisting of:
(a) hydroxy, $C_{1-6}$ alkoxy, or $C_{1-6}$ alkylamino;
(b) $C_{3-6}$ alkenyloxy, or $C_{3-6}$ alkenylamino; and
(c) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl)piperazino, 4-N—($C_{1-6}$ alkylamino-$C_{1-6}$ alkyl)piperazino, or 4-N—($C_{1-6}$ alkylamino-$C_{3-6}$ alkenyl)piperazino;

(ii) trans-2-cyano ethenyl, trans-2-alkylsulfonyl ethenyl, trans-2-alkenylsulfonyl ethenyl, trans-2-substituted alkylsulfonyl ethenyl, and trans-2-substituted alkenylsulfonyl ethenyl, wherein the substituents are selected from the group consisting of:
  (a) hydroxy, $C_{1-6}$ alkoxy, or $C_{1-6}$ alkylamino;
  (b) $C_{3-6}$ alkenyloxy, or $C_{3-6}$ alkenylamino; and
  (c) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl)piperazino, 4-N—($C_{1-6}$ alkylamino-$C_{1-6}$ alkyl)piperazino, or 4-N—($C_{1-6}$ alkylamino-$C_{3-6}$ alkenyl)piperazino;

(iii) $C_{1-6}CO_2R_5$, trans-CH=CHCO$_2$R$_5$, $C_{1-6}$CONHR$_5$, or trans-CH=CHCONHR$_5$, wherein R$_5$ is $C_{1-6}$ alkoxy-$C_{2-6}$ alkyl, amino-$C_{2-6}$ alkyl, $C_{1-6}$ alkylamino-$C_{2-6}$ alkyl, di($C_{1-6}$ alkyl)amino-$C_{2-6}$ alkyl, $C_{1-6}$ alkylthio-$C_{2-6}$ alkyl, substituted $C_{1-6}$ alkoxy-$C_{2-6}$ alkyl, substituted $C_{1-6}$ alkylamino-$C_{2-6}$ alkyl, di(substituted $C_{1-6}$ alkyl)amino-$C_{2-6}$ alkyl, or substituted $C_{1-6}$ alkylthio-$C_{2-6}$ alkyl, in which the substituents are selected from the group consisting of pyrrolidino, piperidino morpholino, piperazino, 4-N—$C_{1-6}$ alkylpiperazino, 4-N—$C_{3-6}$ alkenylpiperazino, 4-N—($C_{1-6}$ alkoxy-$C_{1-6}$ alkyl)piperazino, 4-N—($C_{1-6}$ alkoxy-$C_{3-6}$ alkenyl)piperazino, 4-N—($C_{1-6}$ alkylamino-$C_{1-6}$ alkyl)piperazino, 4-N—($C_{1-6}$ alkylamino $C_{3-6}$ alkenyl)piperazino, imidazolyl, oxazolyl, and thiazolyl;

(iv) $C_{1-6}$CONHR$_5$, or trans-CH=CHCONR$_6$R$_7$, wherein R$_6$ and R$_7$ are independently selected from the group consisting of $C_{1-6}$ alkyl, phenyl-$C_{1-6}$ alkyl, $C_{1-6}$ alkoxycarbonylmethyleneoxy, hydroxy-$C_{1-6}$ alkyl, $C_{1-6}$ alkyloxy-$C_{2-6}$ alkyl, amino-$C_{2-6}$ alkyl, $C_{1-6}$ alkylamino-$C_{2-6}$ alkyl, di($C_{1-6}$ alkyl)amino-$C_{2-6}$ alkyl, $C_{1-6}$ alkylthio-$C_{2-6}$ alkyl, substituted $C_{1-6}$ alkoxy-$C_{2-6}$ alkyl, substituted $C_{1-6}$ alkylamino-$C_{2-6}$ alkyl, di(substituted $C_{1-6}$ alkyl)amino-$C_{2-6}$ alkyl, substituted $C_{1-6}$ alkylthio-$C_{2-6}$ alkyl, wherein the substituents are selected from the group consisting of pyrrolidino, piperidino, morpholino, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy-$C_{3-6}$ alkenyl)piperazino, 4-N—($C_{1-6}$ alkylamino-$C_{1-6}$ alkyl)piperazino, 4-N—($C_{1-6}$ alkylamino-$C_{3-6}$ alkenyl)piperazino, imidazolyl, oxazolyl, and thiazolyl;

(v) R$_7$—C(O)—$C_{1-6}$ alkyl or R$_7$—C(O)—$C_{2-6}$ alkenyl, in which R$_7$ is defined as above in [B(iv)];

(vi) HO—$C_{1-6}$ alkyl-$C_{2-6}$ alkenyl, R$_7$—O—$C_{1-6}$ alkyl-$C_{2-6}$ alkenyl, R$_7$NH—$C_{1-6}$ alkyl-$C_{2-6}$ alkenyl, R$_6$R$_7$N—$C_{1-6}$ alkyl-$C_{2-6}$ alkenyl, R$_7$NH—C(O)—O—$C_{1-6}$ alkyl-$C_{2-6}$ alkenyl, R$_6$R$_7$N—C(O)—O—$C_{1-6}$ alkyl-$C_{2-6}$ alkenyl, R$_7$O—C(O)—O—$C_{1-6}$ alkyl-$C_{2-6}$ alkenyl, or R$_7$—C(O)—O—$C_{1-6}$ alkyl-$C_{2-6}$ alkenyl, wherein R$_6$ and R$_7$ is defined as above in [B(iv)]; and (vii) R$_7$—O—$C_{0-3}$ alkyl-$C_{3-6}$ cycloalk-1-yl, R$_7$NH—$C_{0-3}$ alkyl-$C_{3-6}$ cycloalk-1-yl, R$_6$R$_7$N—$C_{0-3}$ alkyl-$C_{3-6}$ cycloalk-1-yl, R$_7$NH—C(O)—O—$C_{0-3}$ $C_{3-6}$ cycloalk-1-yl, R$_6$R$_7$N—C(O)—O—$C_{0-3}$ alkyl-$C_{3-6}$ cycloalk-1-yl, R$_7$O—C(O)—O—$C_{0-3}$ alkyl-$C_{3-6}$ cycloalk-1-yl, R$_7$—C(O)—O—$C_{0-3}$ alkyl-$C_{3-6}$ cycloalk-1-yl, R$_7$O—C(O)—O—Co-3 alkyl-$C_{3-6}$ cycloalk-1-yl, wherein R$_7$ and R$_6$ are defined as above in [B(iv)];

R$_2$ and R$_3$ are each independently selected from the group consisting of:

(viii) hydrogen, halo, trihalomethyl, $C_{1-6}$ alkyl, substituted $C_{1-6}$ alkyl, $C_{2-6}$ alkenyl, substituted $C_{2-6}$ alkenyl, $C_{1-6}$ alkyloxy, substituted $C_{1-6}$ alkyloxy, $C_{3-6}$ alkenyloxy, substituted $C_{3-6}$ alkenyloxy, $C_{1-6}$ alkylamino, substituted $C_{1-6}$ alkylamino, $C_{3-4}$ alkenylamino, or substituted $C_{3-6}$ alkenylamino; and (ix) mono-, di-, or tri-substituted phenyl wherein the substituents are independently selected from the group consisting of:
  (a) halo, trifluoromethyl, or substituted $C_{1-6}$ alkyl;
  (b) $C_{1-6}$ alkyloxy, substituted $C_{1-6}$ alkyloxy, $C_{3-6}$ alkenyloxy, substituted $C_{3-6}$ alkenyloxy;
  (c) $C_{1-6}$ alkyl-amino, di($C_{1-6}$ alkyl)amino, substituted $C_{1-6}$ alkyl-amino, di(substituted $C_{1-6}$ alkyl)amino, $C_{3-6}$ alkenyl-amino, di($C_{3-6}$ alkenyl)amino, substituted $C_{3-6}$ alkenyl-amino, or di(substituted $C_{3-6}$ alkenyl)amino; and
  (d) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl) piperazino, 4-N—($C_{1-6}$ alkylamino $C_{1-6}$ alkyl)piperazino, or 4-N—($C_{1-6}$ alkylamino $C_{3-6}$ alkenyl)piperazino;

wherein the substituents for (a), (b), (c), and (d) are selected from the group consisting of:
  (1) hydrogen, hydroxy, halo, or trifluoromethyl;
  (2) $C_{1-6}$ alkylalkoxy, $C_{1-6}$ alkylamino, or $C_{1-6}$ alkylthio;
  (3) $C_{3-6}$ alkenyloxy, $C_{3-6}$ alkenylamino, or $C_{3-6}$ alkenylthio; and
  (4) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl) piperazino, 4-N—($C_{1-6}$ alkylamino $C_{1-6}$ alkyl)piperazino, or 4-N—($C_{1-6}$ alkylamino $C_{3-6}$ alkenyl)piperazino;

with the proviso that a) at least one of R$_2$ and R$_3$ is selected from [B (ix)] and wherein the substituents are selected from [B (ix) (b)-(d)] above; or b) R$_2$ and R$_3$ are taken together to form an optionally substituted aryl group, wherein the substituents are defined as above in [B (ix) (a)-(d)];

and R$_4$ is selected from the group consisting of:
(i) hydrogen;
(ii) substituted $C_{1-11}$ alkyl or $C_{2-11}$ alkenyl wherein the substituents are independently selected from the group consisting of:
  (a) hydrogen, hydroxy, $C_{1-6}$ alkyloxy, $C_{1-6}$ alkylthio, $C_{1-6}$ alkylamino, phenyl-$C_{1-6}$ alkylamino, or $C_{1-6}$ alkoxycarbonyl;
  (b) substituted $C_{1-6}$ alkyloxy, $C_{3-6}$ alkenyloxy, or substituted $C_{3-6}$ alkenyloxy;
  (c) di($C_{1-6}$ alkyl)amino, substituted $C_{1-6}$ alkyl-amino, di(substituted $C_{1-6}$ alkyl)amino, $C_{3-6}$ alkenyl-amino, di($C_{3-6}$ alkenyl)amino, substituted $C_{3-6}$ alkenyl-amino, or di(substituted $C_{3-6}$ alkenyl)amino; and
  (d) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl)piperazino, 4-N—($C_{1-6}$ alkylamino $C_{1-6}$ alkyl)piperazino, or 4-N—($C_{1-6}$ alkylamino $C_{3-6}$ alkenyl)piperazino; and (iii) aryl $C_{0-11}$ alkyl wherein the aryl group is selected from phenyl, imidazolyl, furyl, or thienyl.

In some embodiments of the invention, the compound of Formula 1a is a compound wherein R$_1$ is selected from the group consisting of mono-, di-, and tri-substituted aryl-$C_{0-6}$ alkyl wherein aryl is selected from the group consisting of phenyl and thienyl, and the substituents are selected from the group consisting of:

(a) $C_{1-6}CO_2R_5$, trans-CH=CHCO$_2$R$_5$, $C_{1-6}$CONHR$_5$, or trans-CH=CHCONHR$_5$;

(b) $C_{1-6}$CONR$_6$R$_7$, or trans-CH=CHCONR$_6$R$_7$;

(c) R$_7$C(O)C$_{1-6}$ alkyl or R$_7$C(O)C$_{2-6}$ alkenyl; and (d) HO—C$_{1-6}$ alkyl-C$_{2-6}$ alkenyl, R$_7$—O—C$_{1-6}$ alkyl-C$_{2-6}$ alkenyl, R$_7$NH—C$_{1-6}$ alkyl-C$_{2-6}$ alkenyl, R$_6$R$_7$N—C$_{1-6}$ alkyl-C$_{2-6}$ alkenyl, R$_7$NH—C(O)—O—C$_{1-6}$ alkyl-C$_{2-6}$ alkenyl, R$_6$R$_7$N—C(O)—O—C$_{1-6}$ alkyl-C$_{2-6}$ alkenyl, R$_7$O—C(O)—O—C$_{1-6}$ alkyl-C$_{2-6}$ alkenyl, or R$_7$—C(O)—O—C$_{1-6}$ alkyl-C$_{2-6}$ alkenyl.

In other embodiments, the compound of Formula 1a is a compound wherein R$_1$ is selected from the group consisting of mono-, di-, and tri-substituted aryl-C$_{0-6}$ alkyl wherein aryl is selected from the group consisting of phenyl and thienyl, and the substituents are selected from the group consisting of:

(a) $C_{1-6}CO_2R_5$, trans-CH=CHCO$_2$R$_5$, $C_{1-6}$CONHR$_5$, or trans-CH=CHCONHR$_5$;

(b) $C_{1-6}$CONR$_6$R$_7$, or trans-CH=CHCONR$_6$R$_7$;

(c) R$_7$C(O)C$_{1-6}$ alkyl or R$_7$C(O)C$_{2-6}$ alkenyl; and (d) HO—C$_{1-6}$ alkyl-C$_{2-6}$ alkenyl, R$_7$—O—C$_{1-6}$ alkyl-C$_{2-6}$ alkenyl, R$_7$NH—C$_{1-6}$ alkyl-C$_{2-6}$ alkenyl, R$_6$R$_7$N—C$_{1-6}$ alkyl-C$_{2-6}$ alkenyl, R$_7$NH—C(O)—O—C$_{1-6}$ alkyl-C$_{2-6}$ alkenyl, R$_6$R$_7$N—C(O)—O—C$_{1-6}$ alkyl-C$_{2-6}$ alkenyl, R$_7$O—C(O)—O—C$_{1-6}$ alkyl-C$_{2-6}$ alkenyl, or R$_7$—C(O)—O—C$_{1-6}$ alkyl-C$_{2-6}$ alkenyl.

In various embodiments of the invention, the compound of Formula 1a is a compound wherein R$_1$ is selected from the group consisting of mono-, di-, and tri-substituted aryl-C$_{0-6}$ alkyl wherein aryl is selected from the group consisting of phenyl and thienyl, and the substituents are HO—C$_{1-6}$ alkyl-C$_{2-6}$ alkenyl, R$_7$—O—C$_{1-6}$ alkyl-C$_{2-6}$ alkenyl, R$_7$NH—C$_{1-6}$ alkyl-C$_{2-6}$ alkenyl, R$_6$R$_7$N—C$_{1-6}$ alkyl-C$_{2-6}$ alkenyl, R$_7$NH—C(O)—O—C$_{1-6}$ alkyl-C$_{2-6}$ alkenyl, R$_6$R$_7$N—C(O)—O—C$_{1-6}$ alkyl-C$_{2-6}$ alkenyl, R$_7$O—C(O)—O—C$_{1-6}$ alkyl-C$_{2-6}$ alkenyl, or R$_7$—C(O)—O—C$_{1-6}$ alkyl-C$_{2-6}$ alkenyl.

In other embodiments, R$_1$ is selected from the group consisting of mono-, di-, and tri-substituted aryl-C$_{0-6}$ alkyl wherein the aryl-C$_{0-6}$ alkyl is phenyl-C$_{0-6}$ alkyl. In some embodiments, R$_1$ is selected from the group consisting of mono-, di-, and tri-substituted aryl-C$_{0-6}$ alkyl wherein the aryl-C$_{0-6}$ alkyl is aryl-C$_0$alkyl, which is aryl with no alkyl group attached directly to aryl.

In various embodiments, R$_2$ and R$_3$ are each independently selected from the group consisting of: mono-, di-, and tri-substituted phenyl wherein the substituents are independently selected from the group consisting of:

(i) C$_{1-6}$ alkyloxy, substituted C$_{1-6}$ alkyloxy, C$_{3-6}$ alkenyloxy, or substituted C$_{3-6}$ alkenyloxy;

(ii) C$_{1-6}$ alkyl-amino, di(C$_{1-6}$ alkyl)amino, substituted C$_{1-6}$ alkyl-amino, di(substituted C$_{1-6}$ alkyl)amino, C$_{3-6}$ alkenyl-amino, di(C$_{3-6}$ alkenyl)amino, substituted C$_{3-6}$ alkenyl-amino, or di(substituted C$_{3-6}$ alkenyl)amino, and (iv) pyrrolidino, piperidino, morpholino, imidazolyl, substituted imidazolyl, piperazino, 4-N—C$_{1-6}$ alkylpiperazino, 4-N—C$_{3-6}$ alkenylpiperazino, 4-N—(C$_{1-6}$ alkoxy C$_{1-6}$ alkyl)piperazino, 4-N—(C$_{1-6}$ alkoxy C$_{3-6}$ alkenyl)piperazino, 4-N—(C$_{1-6}$ alkylamino C$_{1-6}$ alkyl)piperazino, or 4-N—(C$_{1-6}$ alkylamino C$_{3-6}$ alkenyl)piperazino.

In some embodiments, R$_2$ and R$_3$ are each independently selected from the group consisting of: mono-, di-, and tri-substituted phenyl wherein the substituents are independently selected from the group consisting of C$_{1-6}$ alkyl-amino, di(C$_{1-6}$ alkyl)amino, substituted C$_{1-6}$ alkyl-amino, di(substituted C$_{1-6}$ alkyl)amino, C$_{3-6}$ alkenyl-amino, di(C$_{3-6}$ alkenyl)amino, substituted C$_{3-6}$ alkenyl-amino, and di(substituted C$_{3-6}$ alkenyl)amino.

In some embodiments, R$_4$ is hydrogen.

In some embodiments, the compound of Formula 1a is a compound of Formula 1b:

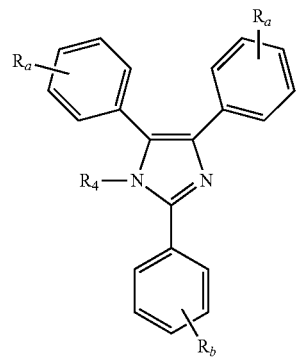

Formula 1b wherein each instance of R$_a$ is independently C$_{1-6}$ alkyl-amino, di(C$_{1-6}$ alkyl)amino, substituted C$_{1-6}$ alkyl-amino, di(substituted C$_{1-6}$ alkyl)amino, C$_{3-6}$ alkenyl-amino, di(C$_{3-6}$ alkenyl)amino, substituted C$_{3-6}$ alkenyl-amino, or di(substituted C$_{3-6}$ alkenyl)amino; and R$_b$ is HO—C$_{1-6}$ alkyl-C$_{2-6}$ alkenyl, R$_7$—O—C$_{1-6}$ alkyl-C$_{2-6}$ alkenyl, R$_7$NH—C$_{1-6}$ alkyl-C$_{2-6}$ alkenyl, R$_6$R$_7$N—C$_{1-6}$ alkyl-C$_{2-6}$ alkenyl, R$_7$NH—C(O)—O—C$_{1-6}$ alkyl-C$_{2-6}$ alkenyl, R$_6$R$_7$N—C(O)—O—C$_{1-6}$ alkyl-C$_{2-6}$ alkenyl, R$_7$O—C(O)—O—C$_{1-6}$ alkyl-C$_{2-6}$ alkenyl, or R$_7$—C(O)—O—C$_{1-6}$ alkyl-C$_{2-6}$ alkenyl.

In some embodiments, the compound of Formula 1 or 1a (such as a compound of Formula 1b or 2), is in the form of a free compound or as its pharmaceutically-acceptable prodrug, metabolite, analogue, derivative, solvate or salt, and is selected from the group consisting of: (2-[4-(3-ethoxy-1-propenyl)phenyl]-4,5-bis(4-(2-propylamino)phenyl)-1H-imidazole; 2-[4-(3-ethoxy-trans-1-pro-pen-1-yl)phenyl]-4,5-bis(4-N,N-diethylaminophenyl)imidazole; 2-[4-(3-ethoxy-trans-1-propen-1-yl)phenyl]-4-(4-N,N-diethylaminophenyl)-5-(4-N-methylaminophenyl)imidazole; 2-[4-(3-methoxy-trans-1-propen-1-yl)phenyl]-4,5-bis(4-pyrrolidinophenyl)imidazole; 2-[4-(3-ethoxy-trans-1-prop-en-1-yl)phenyl]-4,5-bis(4-pyrrolidinophenyl)imidazole; 2-[4-(3-ethoxy-trans-1-propen-1-yl)phenyl]-4-(4-N-dimethylaminophenyl)-5-(4-pyrrolidinophenyl)imidazole; 2-[4-(3-ethoxy-trans-1-propen-1-yl)phenyl]-4-(4-N-methylaminophenyl)-5-(4-pyrrolidino-phenyl) imidazole; 2-[4-(3-ethoxy-trans-1-propen-1-yl)phenyl]-4,5-bis(4-N-morpholinophenyl)imidazole; 2-[4-(3-ethoxy-trans-1-propen-1-yl)phenyl]-4-(4-N-dimethylamin-ophenyl)-5-(4-N-morpholinophenyl)imidazole; 2-[4-(3-ethoxy-trans-1-propen-1-yl)phenyl]-4-(4-N-methylaminophenyl)-5-(4-N-morpholinophenyl)imidazole; and 2-[4-(3-ethoxy-trans-1-propen-1-yl)phenyl]-4-4-N-methylami-nophenyl)-5-(4-N-isopropylaminophenyl)imidazole.

The compound of Formula 1 or 1a can be the specific formulas as described in U.S. Pat. Nos. 5,700,826 and 5,840,721, herein incorporated by reference. Preferred compositions and methods comprise the compound of the following formula (Formula 2):

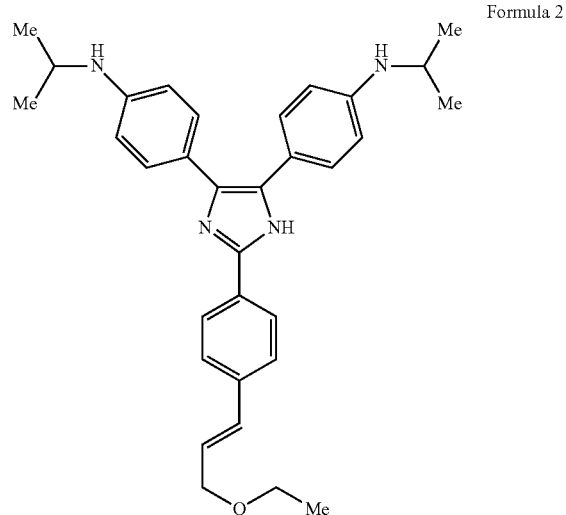 [SMILES: CCOC/C=C/c1ccc(-c2nc(-c3ccc(NC(C)C)cc3)c(-c3ccc(NC(C)C)cc3)[nH]2)cc1]

Formula 2 in the form of a free compound or as its pharmaceutically-acceptable pro-drug, metabolite, analogue, derivative, solvate or salt.

The compounds of Formula 1 or 1a (such as a compound of Formula 1b or 2) are synthesized by any suitable method known in the field. Examples of the synthesis of this class of compounds and the compound of Formula 2, in particular, are disclosed in U.S. Pat. No. 5,840,721, which is hereby incorporated by reference in its entirety.

The compounds of the present invention modulate GSL synthesis and/or metabolism. The compounds can prevent accumulation of complex GSLs. The compounds can inhibit longer chain GSL formation, or complex GSL formation. The compounds can modulate GSL synthesis and/or metabolism by modulating the activity of an ABC transporter involved in GSL biosynthesis. The ABC transporter can be the P-glycoprotein, encoded by the MDR1 gene. MDR1 encodes a 170 kDa membrane alycoporotein (gp-170 or Pgp) that typically acts as an ATP-dependent dfflux pump, transporting a number of unrelated organic compounds out of the cell (Juranka et al., FASEB J. 3:2583-2592 (1989)). The level of expression of gp-170 has been shown to correlate with the degree of drug resistance (Raderer and Sscheitharer, Cancer 72: 3553-3563 (1993)). Gp-170 appears to act as a pump that actively extrudes a wide variety of structurally unrelated compounds, including a full range of antineoplastic drugs. Another ATP-dependent membrane efflux pump, the product of the MRP gene, has also been implicated in the MDR phenomenon (Krishnamachary and Center, Cancer Res. 53:3658-3661 (1993)), as have other ATP-dependent and enzymatic mechanisms.

Drugs of proven antitumor chemotherapeutic value to which MDR has been observed include vinblastine, vincristine, etoposide, teniposide, doxorubicin (adriamycin), daunorubicin, pliamycin (mithramycin), and actinomycin D (Jones et al., Cancer (Suppl) 72:3484-3488 (1993)). Many tumors are intrinsically multidrug resistant (e.g., adenocarcinomas of the colon and kidney) while other tumors acquire MDR during the course of therapy (e.g., neuroblastomas and childhood leukemias). Recently, it has been shown that MDR cells, as opposed to drug-sensitive cells, display increased levels of glucosylceramide (Lavie et al., J. Biol. Chem. 271:19530-19536271:19530-19536 (1996)) and further MDR modulators may increase the cellular susceptibility to chemotherapeutic agents through regulation of ceramide metabolism in cancer cells (Lavie et al., J. Biol. Chem. 272:1682-1687 (1997)). Accumulation of glucosylceramide (GlcCer), a simple glycosylated form of ceramide, is a characteristic of some MDR cancer cells and tumors derived from patients who are less responsive to chemotherapy (Lavie et al., J. Biol. Chem. 271:19530-19536 (1996); Lucc et al., Anticarcer Res. 18: 475-480 (1998)). Modification of ceramide metabolism, by blocking the glycosylation pathway, has been shown to increase cancer cell sensitivity to cytotoxics (Lucci et al., Int. J. One. 15: 541-546 (1999); Lavie et al., J. Biol. Chem. 272: 1682-1687 (1997); Lucci et al., Cancer 86:299-310 (1999)). Further, drug combinations that enhance ceramide generation and limit glycosylation have been shown to enhance kill in cancer cell models (Lavie et al., J. Biol. Chem. 272:1682-1687 (1997); Lucci et al., Cancer 86:299-310 (1999)). Other work has shown that ceramide toxicity can be potentiated in experimental metastasis of murine Lewis lung carcinoma and human neuroepithelioma cells by inclusion of a glucosylceramide synthase inhibitor (Inokuchi et al., Cancer Res. 50: 6731-6737 (1990); Spinedi et al., Cell Death Differ. 5:785-791 (1998)).

Compounds described herein can modulate GSL levels by effecting MDR1 activity. The compounds can provide increased specificity for modulating GlcCer levels, as compared to modulating MDR. For example, a variety of structurally diverse agents have been identified which can restore partly or sometimes completely the normal drug sensitivity to some MDR tumor cells. These chemosensitizers are effective as a result of their ability to interfere with gp-170, causing a reversal in the increase in drug efflux, but among these agents are calcium channel blockers (e.g., verapamil), calmodulin inhibitors (e.g., trifluoperazine), antibiotica (e.g., erythromycin), cardiovascularagents (e.g., quinidine), noncytotoxic analogs of anthracyclines and vinca alkaloids, cyclosporin A and analogs thereof, FK-506 and analogs thereof, and derivatives of cyclopeptides (Lum et al., Cancer (Suppl) 72:3502-3514 (1993)). Many of these agents have not provided a significant contribution to the chemotherapeutic index for the treatment of cancer due to their significant pharmacologidal effects on other organ systems. Compounds of the present invention may be specific for the translocation or flippase activity of the MDR1 that affects GSL synthesis, rather than the reversal of MDR, and may also have a lack of significant toxicity and other nonspecific pharmacological effects. Alternatively, compounds may affect both, but have a greater effect on GSL levels rather than MDR.

For example, cells exhibiting abnormal GSL metabolism can be treated with the compounds of the present invention at a concentration or dosage that modulates GlcCer levels, but would not affect MDR in cancer cells. The compound administered to subjects suffering from GSL metabolism disorders can ameliorate symptoms of GSL disorder, but not MDR of subjects suffering from cancer. Therapeutically effective dosages of the compounds of the present invention can have an effect on GSL disorder symptoms, but not on MDR. In some embodiments, the compounds may specifically modulate the levels of specific GSL, for example neutral GSLs or acidic GSLs, or both, in which other MDR inhibitors do not. The compounds can have a higher specificity or increased activity in affecting GSL as compared to other MDR inhibitors, and thus more effective in treating GSL metabolism disorders. Dosages and toxicities can also vary between compounds that are used for treating GSL disorders as compared to compounds used in treating MDR with MDR1 inhibitors.

Combinations of compounds of the present invention are also provided. In preferred embodiments, combinations have a synergistic effect. The present invention contemplates administering the compounds with any of several different kinds of compounds. These include, for example, substrate competitors for enzyme inhibition therapy, enzymes for enzyme replacement therapy, gene therapy and chaperones for enzymes. For example, a composition of the present invention can comprise a first compound of Formula 1 or 1a as described herein (for example, a compound of Formula 1b or 2), with a second compound that is a glucosylceramide synthase inhibitor. In some embodiments, the glucosylceramide synthase inhibitor is miglustat, or, 1-butyl-2-(hydroxymethyl)piperidine-3,4,5-triol. Another compounds that can be used is PDMP (1R-phenyl-2R-decanoylamino-3-morpholino-1-propanol), previously identified as the D-threo isomer (Inokuchi et al., *J. Lipid Res.* 28:565-571 (1987)), that has been found to produce a variety of chemical and physiological changes in cells and animals (Radin et al., "Use of 1-Phenyl-2-Decanoylamino-3-Morpholino-1-Propanol (PDMP), an Inhibitor of Glucosylceramide Synthesis," In NeuroProtocols, A Companion to Methods in Neurosciences, S. K. Fisher et al., Ed., (Academic Press, San Diego) 3:145-155 (1993) and Radin et al., "Metabolic Effects of Inhibiting Glucosylceramide Synthesis with PDMP and Other Substances," In Advances in Lipid Research; Sphingolipids in Signaling, Part B., R. M. Bell et al., Ed. (Academic Press, San Diego) 28:183-213 (1993)). Homologs, analogs, or derivatives of PDMP can also be used, such as the P4 compound (1-phenyl-2-palmitoylamino-3-pyrrolidino-1-propanol). (Shayman et al., *J. Biol. Chem.*, 277:18447-18453 (2002); Asano, *Glycobiology* 13:93R-104R (2003); Jimbo et al., J. Biochem. (Tokyo) 127:485-491 (2000)). Imino sugar-based glucosylceramide synthase inhibitors, such as N-butyldeoxynojirimycin, may also be used.

In some embodiments, treatment of GSL disorders comprise administering compositions comprising the compound of the present invention along with enzyme-replacement therapy (ERT), for example with imiglucerase (an analogue of human (β-glubcocerebrosidase) or α-galactosidase (Brady, *Acta Paediatr. Suppl.* 92:19-24 (2003); Heukamp et al., *Pathol. Res. Pract.* 199:159-163 (2003); Wilcox et al., *Am. J. Hum. Genet.* 75:(65-74) (2004)). Combinatorial treatments also include gene therapy, for example, a patient with Fabry disease can be treated with a recombinant retrovirus carrying the cDNA encoding the defective α-Gal A that is used to transfect skin fibroblasts obtained from the Fabry patient (Medin et al., *Proc. Natl. Acad. Sci. USA* 93:7917-7922 (1996)) along with the compound of the present invention.

In another embodiment, the compound of Formula 1 or 1a (such as a compound of Formula 1b or 2) is administered in combination with a chaperone. Chaperones have an important role in protein folding. Misfolded proteins are typically eliminated by cellular quality control mechanisms, or accumulate and affect protein trafficking. Artificial chaperones used in combination with the compound of the present invention include non-specific chemical chaperones, such as high concentrations of glycerol, dimethylsulfoxide, trimethylamine N-oxide, or deuterated water have been shown to stabilize the mutant protein and increase the intracellular trafficking of mutant protein in several diseases (Brown et al., *Cell Stress Chaperones* 1:117-125 (1996); Burrows et al., *Proc. Natl. Acad. Sci. USA;* 97:1796-1801 (2000)). Pharmacological chaperones which bind to the enzyme and promote trafficking of the enzyme from the endoplasmic reticulum to the lysosome can be used. In preferred embodiments, the compound of Formula 1 is adminstered with active site specific chaperones (ASSC). ASSCs known in the art, such as 1-deoxygalactonojirimycin (DGJ) (U.S. Pat. Nos. 6,274,597, and 6,774,135), can be used. ASSCs are thought to stabilize misfolded proteins thus, enabling proper protein conformation for trafficking to the lysosomes, and thus ASSCs aid in ameliorating LSDs (U.S. Pat. Nos. 6,583,158, 6,589,964, 6,599,919). Other ASSCs include glucoimidazole (GIZ) and polyhydroxycyclohexenyl amine (PHCA) derivatives (U.S. Pat. Appln. No. 20050137223), which may be used in combination with the compound of the present invention for treqating diseases associated with mutant glucocerebrosidase, such as Gaucher's. Hydroxy piperidine (HP) derivatives (U.S. Pat. Appln. 20050130972) can also be used in combination with the compound of Formula 1 or 1a (for example, a compound of Formula 1b or 2), in treating individuals having Gaucher disease.

II. Conditions Characterized by Disorders in GSL Metabolism

The importance of treating GSL metabolism disorders is underscored by various important roles sphingolipids have. Sphingolipids are ubiquitous constituents of membrane lipids in mammalian cells. Sphingolipids are involved in membrane trafficking and intracellular signaling as a factor requiring for the formation of membrane micro domains so called lipid rafts. In addition to being the building blocks of biological membranes, glycosphingolipids appear to be involved in cell proliferation (Hannun and Bell, *Science,* 243:500-507 (1989)) differentiation (Schwarz et al., *J. Biol. Chem.* 270: 10990-10998 (1995); Harel and Futerman, *J. Biol. Chem.* 268:14476-14481 (1993)), oncogenic transformation (Hakomori, *Annu. Rev. Biochem.* 50:733-764 (1981); Morton et al., *Prog. Brain Res.* 101:251-275 (1994)) and the prevention of the onset of apoptosis (Nakamura et al., *J. Biol. Chem.* 271: 1255-1257 (1996)).

The biosynthesis process of sphingolipids in mammalian cells may be as illustrated in FIG. 1. The first step depicts the condensation reaction of L-serine with palmitoyl CoA. The reaction is catalyzed by serine palmitoyl transferase to generate 3-ketodihydrosphingosine. The resulting 3-ketodihydrosphingosine is then reduced to dihydrosphingosine. The obtained dihydrosphingosine can then undergo N-acylation followed by desaturation to generate ceramide (Cer). These reactions to produce Cer typically occur on the cytosolic surface of the endoplasmic reticulum (ER). Cer is then thought to be delivered to the lumenal side of the Golgi apparatus and converted to sphingomyelin (SM) by SM synthase catalyzing transfer of phosphocholine from phosphatidylcholine (PC) to Cer. Cer is also converted to glucosylceramide (GlcCer). Glucosylceramides are produced by glucosylceramide synthase (GCS) transferring glucose from UDP-glucose to ceramide (Basu, et al., (1968) *J. Biol. Chem.* 243:5802-5804). The rate of GlcCer formation under physiological conditions usually depends on the tissue level of UDP-glucose, which in turn depends on the level of glucose in a particular tissue (Zador et al., *J. Clin. Invest.* 91:797-803 (1993)). In vitro assays based on endogenous ceramide typically yield lower synthetic rates than mixtures containing added ceramide, suggesting that tissue levels of ceramide are also normally rate-limiting (Brenkert et al., *Brain Res.* 36.183-193 (1972)).

However, unlike many other GSLs, GlcCer is typically made on the outer leaflet of the Golgi bilayer (Lannert et al., *J. Biol. Chem.* 273:2939-2946 (1998)). As a result, for GlcCer to be accessed by glycosyltransferases for further carbohydrate elongations, GlcCer typically needs to be translocated, or "flipped", into the lumen of the Golgi. MDR1 can function as a glycolipid flippase and appears to be responsible for the translocation of GlcCer into the lumen for further carbohydrate elongation. MDR1 translocation appears to be specific for neutral GSL synthesis (DeRosa et al., *J. Biol. Chem.* 279:7867-7876 (2004)). Compounds of the present invention can specifically inhibit the translocation or flippase function of MDR1, or may be specific for modulating neutral GSL synthesis, acidic GSL synthesis, or both. For example, the compound can inhibit Gb3 accumulation but not gangliosides, whereas other compounds inhibit accumulation of both Gb3 and gangliosides.

Most glycosphingolipids (GSLs) are derived from glucosylceramide (GlcCer). GSLs are a subtype of glycolipids containing the amino alcohol sphingosine, and include cerebrosides, gangliosides, and globosides. Cerebrosides are important components of animal and muscle nerve cells, and include myelin. Gangliosides are GSLs with one or more sialic acids, common gangliosides being GD1a, GD1b, GD2, GD3, GM1, GM2, GM3, and GT1b. Gangliosides are a component of the plasma membrane and modulate cell signal transduction events. They are also present in lipid rafts. Globosides are GSLs with N-acetyglactosamine as the side chain. Sphingomyelin is present in animal cell membranes and may have a role in signal transduction. Defects in the metabolism of GSLs can lead to different diseases, for example, a defect in the degradation of glucocerebrosides can cause Gacuher's, defect in galactocerebrosides can cause Karbbe disease. Gangliosides are imported in immunology and may be involved in neurodegenerative diseases. Defects in β-hexosadmimidase, which cleaves the side chain of globosides, can lead to Sandhoff disease, and sphingomyelin accumulation can lead to Niemann-Pick disease.

The compositions and methods described herein are effective in treating GSL metabolic conditions, which may specifically inhibit the translocation or flippase function of MDR1, or may be specific for modulating neutral GSL synthesis. In some aspects, conditions due to any defective enzyme, or abnormal levels of substrates/products of the GSL biosynthesis pathways, may be treated. Conditions include Gaucher (GlcCer accumulation) and Fabry (globotraiosyl, or Gb3, accumulation), as well as other lysosomal storage diseases including, but not limited to, Niemann-Pick, Tay Sachs, and Sandhoff's disease. Other diseases with impaired glycosylated proteins, such as cystic fibrosis, can also be treated by compositions and methods of the present invention.

Many known lysosomal storage diseases (LSDs) involve a similar pathogenesis, namely, a compromised lysosomal hydrolase. Generally, LSDs are due to genetic deficiencies in glycoconjugate catabolism, which may be due to the activity of a single lysosomal hydrolytic enzyme, such as a specific lysosomal sugar hydrolase or its activator protein, being reduced or lacking altogether. The substrate of the compromised enzyme accumulates undigested in lysosomes, producing severe disruption of cellular architecture and various disease manifestations. A number of sphingolipidoses, group of LSDs caused by deficient activity of lysosomal enzymes crucial for the degradation of sphingolipids, is shown in Table 1, and may be treated by the compositions and methods of the present invention. For example, in "glycosphingolipidoses", accumulation typically results in the formation of lipid inclusions and multilamellar structures that prevent normal cell functions. LSDs can be classified by the nature of their storage material, such as lipid storage disorders (including Gaucher's and Nieman-Pick), gangliosidoses (such as Tay-Sachs disease), leukodystrophies, mucopolysaccharidoses (including Hunter syndrome and Hurler disease), glycoprotein storage disorders, and mucolipidoses.

Gaucher's disease is one of the most common lysosomal storage diseases known. Type 1 is usually the most common among three recognized clinical types and typically follows a chronic course which does not involve the nervous system. Types 2 and 3 both have a CNS component, the former typically being an acute infantile form with death by age two and the latter a subacute juvenile form. The incidence of Type 1 Gaucher's disease is about one in 50,000 live births and about one in 400 live births among Ashkenazis (Kolodny et al., 1998, "Storage Diseases of the Reticuloendothelial System", In: Nathan and Oski's Hematology of Infancy and Childhood, 5th ed., vol. 2, David G. Nathan and Stuart H. Orkin, Eds., W. B. Saunders Co., pages 1461-1507). Also known as glucosylceramide lipidosis, Gaucher's disease is typically caused by inactivation of the enzyme glucocerebrosidase and accumulation of glucocerebroside (also known as GlcCer). Glucocerebrosidase normally catalyzes the hydrolysis of glucocerebroside to glucose and ceramide. In Gaucher's disease, glucocerebroside accumulates in tissue macrophages which become engorged and are typically found in liver, spleen and bone marrow and occasionally in lung, kidney and intestine. Secondary hematologic sequelae include severe anemia and thrombocytopenia in addition to the characteristic progressive hepatosplenomegaly and skeletal complications, including osteonecrosis and osteopenia with secondary pathological fractures.

Niemann-Pick disease, also known as sphingomyelin lipidosis, comprises a group of disorders characterized by foam cell infiltration of the reticuloendothelial system. Foam cells in Niemann-Pick become engorged with sphingomyelin and, to a lesser extent, other membrane lipids including cholesterol. Niemann-Pick is typically caused by inactivation of the enzyme sphingomyelinase in Types A and B disease, with 27-fold more residual enzyme activity in Type B. The pathophysiology of major organ systems in Niemann-Pick can be briefly summarized as follows. The spleen is the most extensively involved organ of Type A and B patients. The lungs are involved to a variable extent, and lung pathology in Type B patients is the major cause of mortality due to chronic bronchopneumonia. Liver involvement is variable, but severely affected patients may have life-threatening cirrhosis, portal hypertension, and ascites. The involvement of the lymph nodes is variable depending on the severity of disease. Central nervous system (CNS) involvement differentiates the major types of Niemann-Pick. While most Type B patients do not experience CNS involvement, it is characteristic in Type A patients. The kidneys are only moderately involved in Niemann Pick disease.

Fabry disease is an X-linked recessive LSD characterized by a deficiency of α-galactosidase A (α-Gal A), also known as ceramide trihexosidase, which leads to vascular and other disease manifestations via accumulation of glycosphingolipids with terminal α-galactosyl residues, such as globotriaosylceramide (GL-3, or Gb3) (see generally Desnick R J et al., 1995, α-galactosidase A Deficiency: Fabry Disease, In: The Metabolic and Molecular Bases of Inherited Disease, Scriver et al., eds., McGraw-Hill, New York, 7.sup.th ed., pages 2741-2784). Symptoms may include anhidrosis (absence of sweating), painful fingers, left ventricular hypertrophy, renal manifestations, and ischemic strokes. The severity of symptoms varies dramatically (Grewal, *J. Neurol.* 241:153-15 (1994)). A variant with manifestations limited to the heart is recognized, and its incidence may be more prevalent than once believed (Nakao. *N. Engl. J. Med.* 333:288-293 (1995)).

Tay-Sachs disease, also known as GM2 gangliosidosis or hexosaminidase A deficiency, is a genetic disorder wherein the most common variant, infantile Tay-Sachs disease, is fatal. The disease is typically caused by mutations on the HEXA gene. The HEXA gene encodes the α-subunit of the lysosomal enzyme β-hexosaminidase A. Hydrolysis of GM2-ganglioside typically requires three proteins. two subunits of hexosaminidase A, and a small glycolipid transport protein, the GM2 activator protein (GM2A), which acts as a substrate specific cofactor for the enzyme. Deficiency in any one of these proteins leads to storage of the ganglioside, primarily in the lysosomes of neuronal cells lysosomes of neuronal cells. Deficiencies in hexosaminidase A caused by HEXA mutations can lead to Tay-Sachs disease.

Patients with Sandhoff's disease have similar symptoms to Tay-Sachs. Sandhoff's is a lipid storage disorder that causes progressive destruction of nerve cells. The disease is typically inherited and involves the CNS and involves mutations in the HEXB gene which encodes the β-subunit of the lysosomal enzymes β-hexosaminidase A and B. Thus, HEXB mutations can affect both β-hexosaminidase A and B and prevent breakdown of GM2 gangliosides and other molecules leading to accumulation of these molecules, causing nerve cell destruction and disease.

Diseases and conditions other than LSDs are also treated by the compositions and methods of the present invention. For example, other diseases resulting from, or which result in, increased glycosphingolipid synthesis can be treated, such as cystic fibrosis. Cystic fibrosis (CF) epithelial cells express a greater density of an asialylated ganglioside (gangliotetraosyl ceramide, Gg4), on their apical surface, which manifest as a higher susceptibility of CF individuals of acquiring bacterial infections. (Hart and Winstanley, *British Medical Bulletin* 61:81-96 (2002)).

The compounds of Formula 1 or 1a (such as Formula 1b or 2), can be used to treat other conditions by inhibiting GSL synthesis, such as conditions associated with bacteria. For example, administration of the compounds of the present invention may reduce cell sensitivity, and thus conditions associated with verotoxin (or Shiga toxin), cholera toxin, or uropathic *E. coli*. Verotoxins are thought to inhibit protein synthesis in cells and may have a role in hemorrhagic colitis and hemolytic uremic syndrome, by damaging endothelial cells in the kidney and brain. A component of the verotoxin is believed to inhibit protein synthesis by binding Gb3 and enters the cell. Cholera toxin, believed to be the cause of the major characteristics of cholera, is thought to enter cells by binding GM1. Uropathic *E. coli* may bind globo series GSLs. Without being bound by theory, reducing GSL synthesis may reduce the ability of the toxins, or infectious bacteria, to enter the cell, thereby decreasing their negative effects.

For treatment, the compounds of Formula 1 or 1a (such as a compound of Formula 1b or 2), can be administered before, after, before and after, and/or simultaneously with another compound as described herein. The compounds of Formula 1 or 1a (such as a compound of Formula 1b or 2) can be administered in the form of a free compound or a pharmaceutically-acceptable pro-drug, metabolite, analogue, derivative, solvate or salt are useful in the treatment of conditions related to defective GSL metabolism, such as MDR related LSDs, either separately or in combination with another agent or therapy, such as ERT. These compounds can be administered orally, topically or parenterally in dosage unit formulations containing conventional non-toxic pharmaceutically acceptable carriers, adjuvants, and vehicles. The term parenteral as used herein includes subcutaneous injections, aerosol, intravenous, intramuscular, intrathecal, intracranial, intrasternal injection or infusion techniques.

The present invention also has the objective of providing suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavoring agents, coloring agents and preserving agents in order to produce pharmaceutically elegant and palatable preparations. The tablets contain the acting ingredient in admixture with non-toxic pharmaceutically acceptable excipients that are suitable for the manufacture of tablets. These excipients may be, for example, (1) inert diluents, such as calcium carbonate, lactose, calcium phosphate, carboxymethylcellulose, or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

Administration may be intravenously, intraperitoneally, intramuscularly, subcutaneously, intracavity, or transdermally. For in vitro studies, the compounds may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic\aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, growth factors and inert gases and the like.

Therefore, the present invention encompasses methods for ameliorating diseases and conditions, including but not limited to disorders associated with abnormal or defective GSL synthesis, with a compound of Formula 1 or 1a (such as a compound of Formula 1b or 2), in the form of a free compound or a pharmaceutically-acceptable pro-drug, metabolite, analogue, derivative, solvate or salt, and a chemotherapeutic or pharmaceutical agent in an amount sufficient to inhibit or ameliorate the cell's proliferation or the disorder. Generally, the terms "treating", "treatment" and the like are used herein to mean affecting a subject, tissue or cell to obtain a desired pharmacologic and/or physiologic effect. The effect may be prophylactic in terms of completely or partially preventing a disease or sign or symptom thereof, and/or may be therapeutic in terms of a partial or complete cure for a disorder and/or adverse effect attributable to, for example, aberrant cell proliferation. "Treating" as used herein covers any treatment of, or prevention of a disease or disorder in a vertebrate, a mammal, particularly a human, and includes: (a) preventing the disease or disorder from occurring in a subject that may be predisposed to the disease or disorder, but has not yet been diagnosed as having it; (b) inhibiting the disease or disorder, i.e., arresting its development; or (c) relieving or ameliorating the disease or disorder, i.e., cause regression of the disease or disorder.

The present invention includes various pharmaceutical compositions useful for ameliorating diseases and disorders related to GSL metabolism, including LSDs and the like. The pharmaceutical compositions according to one embodiment of the invention are prepared by bringing a compound of Formula 1 or 1a (such as a compound of Formula 1b or 2), in the form of a free compound or a pharmaceutically-acceptable pro-drug, metabolite, analogue, derivative, solvate or salt, and optionally, one or more pharmaceutical agents or combinations of the compound of Formula 1 or 1a (such as a compound of Formula 1b or 2), into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

The pharmaceutical compositions are preferably prepared and administered in dose units. Solid dose units are tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the present invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249: 1527, (1990); Gilman et al. (eds.) (1990), each of which is herein incorporated by reference. Dosages for parenteral administration of active pharmaceutical agents can be converted into corresponding dosages for oral administration by multiplying parenteral dosages by appropriate conversion factors. As to general applications, the parenteral dosage in mg/m$^2$ times 1.8 may equal the corresponding oral dosage in milligrams ("mg"). See the Miller-Keane Encyclopedia & Dictionary of Medicine, Nursing & Allied Health, 5.sup.th Ed., (W.B. Saunders Co. 1992). pp. 1708 and 1651.

The method by which the compound of Formula 1 or 1a (such as a compound of Formula 1b or 2) may be administered for oral use would be, for example, in a hard gelatin capsule wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil. The active ingredient can be mixed with a co-solvent mixture, such as PEG 400 containing Tween-20. A compound of Formula 1 or 1a (such as a compound of Formula 1b or 2) can also be administered in the form of a sterile injectable aqueous or oleaginous solution or suspension. The compound of Formula 1 or 1a (such as a compound of Formula 1b or 2), can generally be administered intravenously or as an oral dose of 0.5 to 10 mg/kg given every 12 hours, 1 to 3 times a day, or may be given before and 1 to 3 times after the administration of another pharmaceutical agent, with at least one dose 1 to 4 hours before and at least one dose within 8 to 12 hours after the administration of the other agent.

Aqueous suspensions normally contain the active materials in admixture with excipients suitable for the manufacture of aqueous suspension. Such excipients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation, product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents that have been mentioned above. The sterile injectable preparation can be a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

A compound of Formula 1 or 1a (such as a compound of Formula 1b or 2), can also be administered in the form of suppositories for rectal administration of the drug. These compositions can be prepared by mixing the drug with a suitable non-irritating excipient that is solid at ordinary temperature but liquid at the rectal temperature and will therefore melt in the rectum to release the drug. Such materials include cocoa butter and polyethylene glycols.

The compounds of Formula 1 or 1a (such as a compound of Formula 1b or 2), as used in the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

For topical use, creams, ointments, jellies, solutions or suspensions, etc., containing the compounds of Formula 1 or 1a (such as a compound of Formula 1b or 2), may be employed.

Dosage levels of the compounds of Formula 1 or 1a (such as a compound of Formula 1b or 2), as used in the present invention may be of the order of about 0.5 mg to about 20 mg per kilogram body weight, an average adult weighing 70 kilograms, with a preferred dosage range between about 5 mg to about 20 mg per kilogram body weight per day (from about 0.3 gms to about 1.2 gms per patient per day). The amount of the compound of Formula 1 or 1a (such as a compound of Formula 1b or 2) that may be combined with the carrier materials to produce a single dosage will vary depending upon the host treated and the particular mode of administration. For example, a formulation intended for oral administration to humans may contain about 5 mg to 1 g of a compound of Formula 1 or 1a (such as a compound of Formula 1b or 2) with an appropriate and convenient amount of carrier material that may vary from about 5 to 95 percent of the total composition. Dosage unit forms will generally contain between from about 5 mg to 500 mg of Formula 1 or 1a (such as a compound of Formula 1b or 2), of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

In addition, some of the compounds of the instant invention may form solvates with water or common organic solvents. Such solvates are encompassed within the scope of the present invention In further embodiments the invention provides compositions comprising a compound of Formula 1 or 1a (such as a compound of Formula 1b or 2), in the form of pharmaceutically-acceptable pro-drugs, metabolites, analogues, derivatives, solvates or salts in admixture with an active pharmaceutical agent or chemotherapeutic agent, together with a pharmaceutically acceptable diluent, adjuvant, or carrier.

EXAMPLES

Example #1

Effect of Compound of Formula 2 on Cultured Cell GSLs

Figure 2:
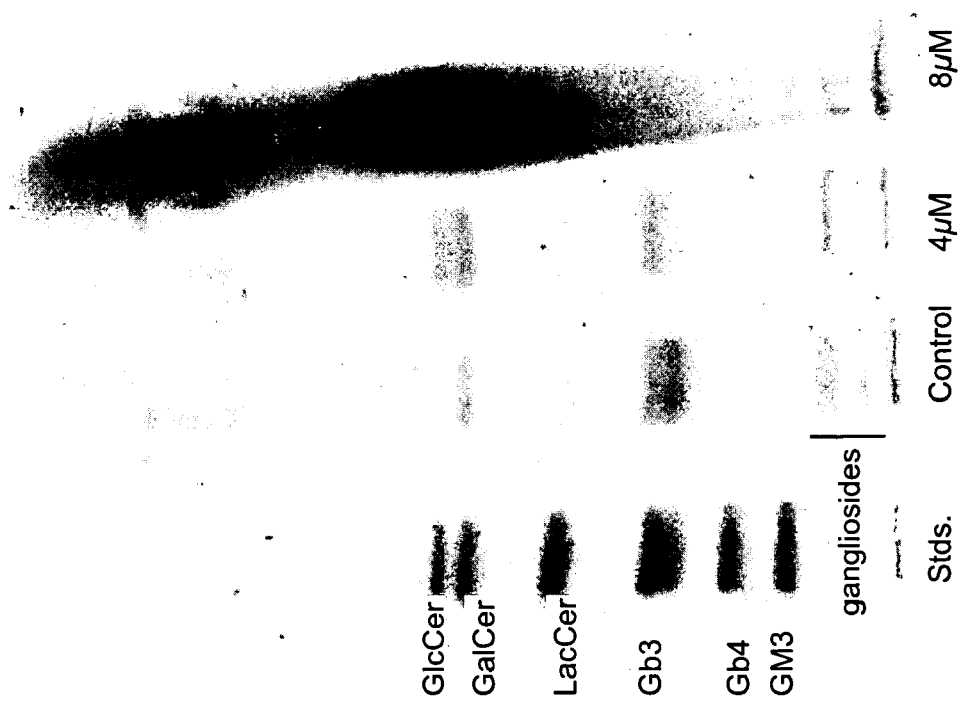
FIG. 2 depicts decrease of longer chain GSL formation after treatment with compositions of the present invention.

Cultured Gaucher and/or Fabry B-cell lines were treated with 0, 4, or 8 µM of the compound of Formula 2 for 3 days. The GSL fractions were purified and separated by thin layer chromatography (TLC). GSL fractions were detected by orcinol spray. (FIG. 2). At 4 µM there was a decrease in Gb3 levels and increased LacCer and GlcCer levels, suggesting translocation of GlcCer into the Golgi was inhibited, preventing longer chain GSL formation and/or increased GSL breakdown into LcCer and GlcCer. At 8 µM, complex GSL levels were significant reduced.

Example #2

Treatment of Fabry Mice with Compound of Formula 2

Eight control neonatal Fabry mice (5 male and 3 female) were injected ip bi-weekly one week from birth with saline, and eight experimental Fabry mice (4 male and 4 female) were injected ip bi-weekly one week from birth with Formula 2 (20 mg/kg) in saline, for a period of 10 weeks. After this time, the mice were euthanized by anaesthetic overdose. Tissues from the mice were removed and frozen for later glycolipid analysis. Samples of each tissue were also frozen in OCT mounting medium and frozen sections of the livers of all animals were processed.

Gb3 expression in the frozen liver sections was determined using VT1 section staining using verotoxin staining (as described in Mattocks et al., *FEBS J.* 273:2064-2075 (2006)), such that the Gb3 positive tissue structures are stained brown and the sections are counter stained with hematoxylin/eosin. All controls sections were similar. Intense staining of the stellate Kupffer cells (see FIG. 3, arrows) as previously reported (Mattocks et al., *FEBS J.* 273:2064-2075 (2006))

TABLE 1

Major Sphingolipidoses

Figure 3:
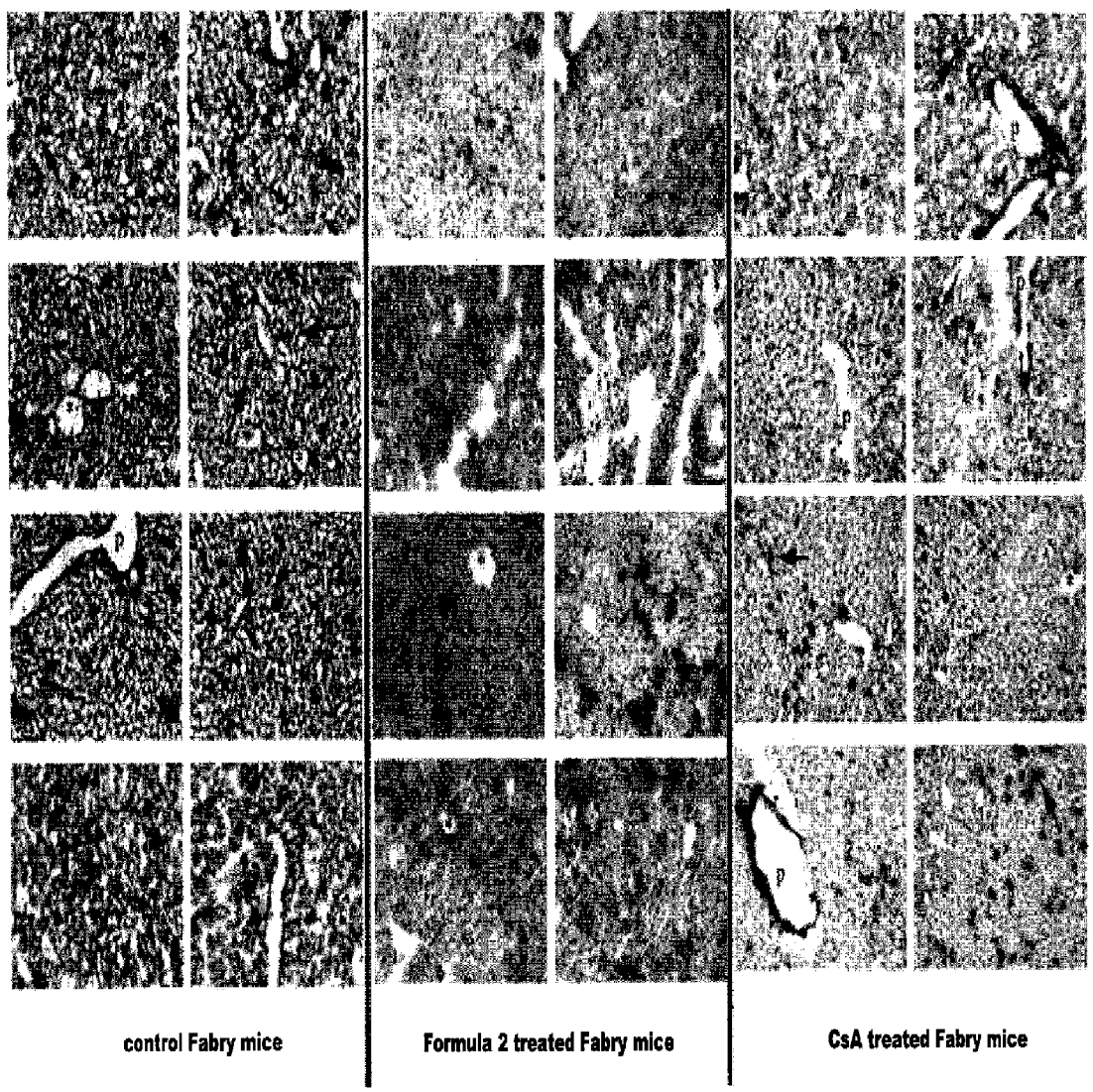
FIG. 3 shows the effect of a compound of Formula 2 on Gb3 accumulation in the Fabry mouse model liver tissue.

| Clinical diagnosis | Affected lipids | Enzyme defect |
| --- | --- | --- |
| GM1 gangliosidosis | GM1 ganglioside Galactose-rich fragments of glycoproteins | β-Galactosidase |
| GM2 gangliosidosis Tay-Sachs disease, B variant | GM2 ganglioside | β-Hexosaminidase A |
| B1 variant | GM2 gaglioside | β-Hexosaminidase |
| AB variant | GM2 gaglioside | GM2 activator protein |
| Sandhoff's disease, O variant | GM2 gaglioside, Asialo GM2 ganglioside, Globoside | β-Hexosaminidase A, B |
| Niemann-Pick disease (A and B) | Sphingomyelin | Sphingomyelinase |
| Gaucher's disease | Glucosylceramide Gluccosylsphingosine | Glucosylceramidase |
| Farber's disease | Ceramide | Acid ceramidase |
| Fabry's disease | Trihexosylceramide | a-Galactosidase A |
| Metachromatic leukodystrophy | Sulfatide | Arylsulfatase A |
| Multiple sulfatase deficiency | Sulfatide and other compounds | Arylsulfatase A, B, C and others |
| Globoid cell leukodystrophy (Krabbe's disease) | Galactosylceramide Galactosylsphingosine | Galactosylceramidase |
| Total SAP deficiency | Multiple sphingolipids | Sphingolipid activator protein |
| SAP-B deficiency | Sulfatide and others | Sulfatidase activator (SAP-B) |
| SAP-C deficiency | Glucosylceramide | SAP-C | was detected together with strong staining of endothelial cells lining the hepatic portal (see FIG. 3, p) and central veins (see FIG. 3, *). In seven of eight of the experimental animals, there was essentially no residual staining for Gb$_3$ within the liver. In one animal, some diffuse Gb3 staining remained but even in this animal, the staining was considerably less than in the control group.

Treating neonatal mice with Formula 2 was more effective in reducing liver Gb3 staining as compared to mice treated with cyclosporine (FIG. 3, Formula 2 treated Fabry mice compared to CsA treated Fabry mice). Kupffer cell staining of mice treated with cyclosporine, although less intense, was still present. Similarly, residual endothelial cell staining (particularly in portal veins which were refractory) in some mice treated with cyclosporine remained in evidence.

Since Kupffer cells are scavenger macrophage-like cells, it is possible that their Gb3 content reflects the level of Gb3 in the serum rather than (or in addition to) endogenous synthesis by the Kupffer cells themselves. As treatment with Formula 2 essentially removed Gb3 from the liver Kupffer cells, the circulating level of Gb3 in these treated mice is likely also reduced to normal background levels.

Figure 4:
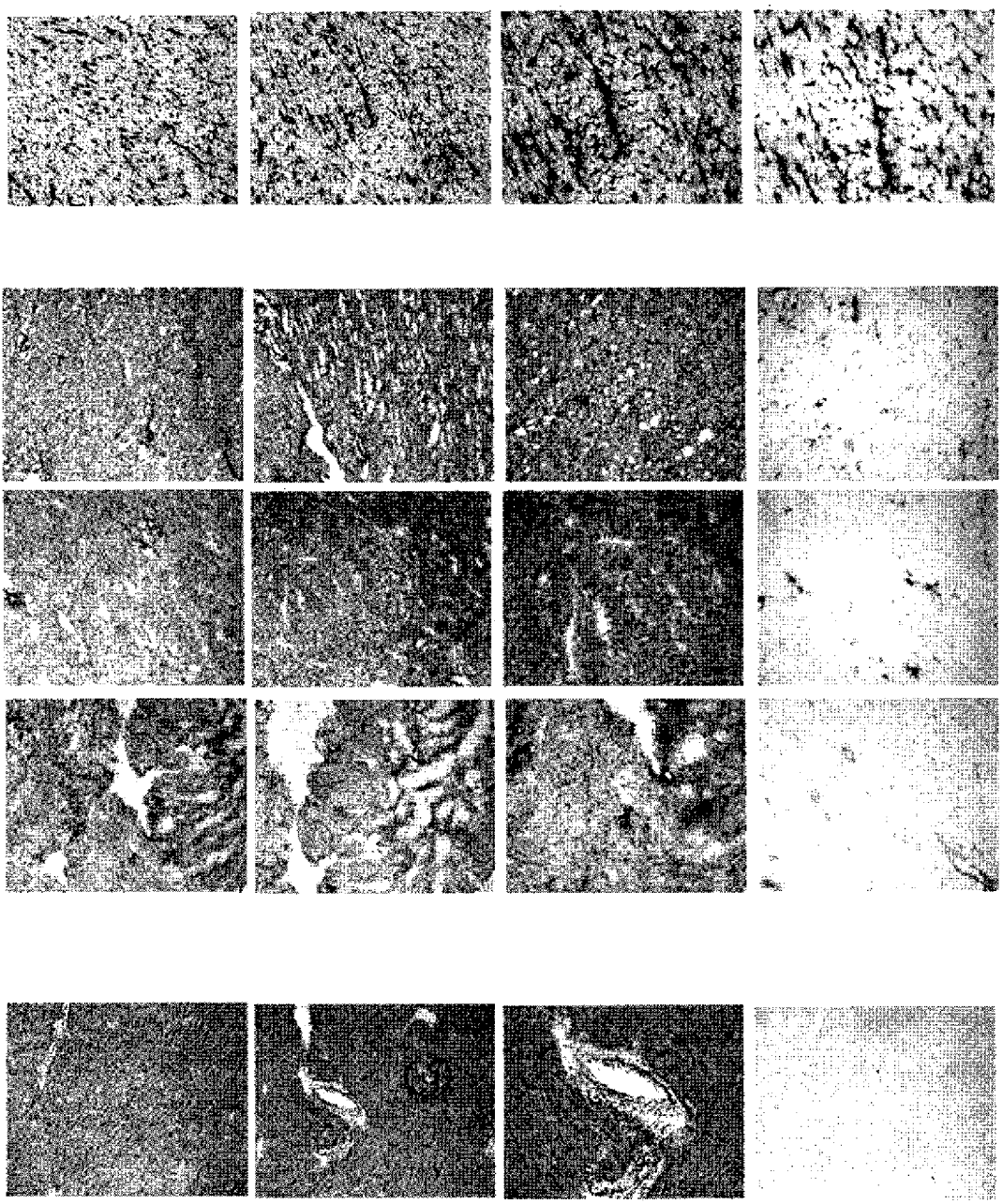
FIG. 4 shows the effect of a compound of Formula 2 on Gb3 accumulation in the Fabry mouse model heart tissue.

Treatment of Fabry mice with Formula 2 was also effective in reducing heart Gb3 staining as shown in FIG. 4. The top row of FIG. 4 illustrates VT1 stained heart tissue from Fabry mouse not treated with compound of Formula 2. The middle three rows of FIG. 4 illustrate heart tissue from Fabry mice that were treated with compound of Formula 2. The bottom row of FIG. 4 illustrates VT1 staining of heart tissue from normal mice. The right most column of panels of FIG. 4 are VT1 staining without hematoxylin/eosin counterstain.

Example #3

Treatment of Fabry Mice with ERT and Compound of Formula 2

Adult Fabry mice are treated intraperitoneally (i.p.) with a bolus injection of α-galactosidase. Half of the mice are used as controls and the other half are injected i.p. with the compound of Formula 2. Serum Gb3 levels are monitored for nine weeks post ERT (typically in ERT mice, serum Gb3 is undetectable until 9 weeks later, when Gb3 levels are recovered) at different time points.

Organs (wild-type, Fabry controls, and Fabry treated) are harvested to determine GSL levels. The GSLs are extracted and levels are determined by TLC-orcinol, and/or metabolic labeling of GSLs. Serum levels of Gb3 may also be determined by VT-1 based ELISA, as Gb3 is the verotoxin (VT) receptor. VT1 staining is typically increased in Fabry mice compared to wild-type mice, and effect of treatment with compound 1 on ERT mice can be determined by VT1 TLC overlay and VT1 staining. Animals treated with the compound may have lower levels of complex GSLs such as Gb3 and increased levels of GlcCer and/or LacCer, and decreased VT1 staining as compared to the controls.

While preferred embodiments of the present invention have been shown and described herein, it will be obvious to those skilled in the art that such embodiments are provided by way of example only. Numerous variations, changes, and substitutions will now occur to those skilled in the art without departing from the present invention. It should be understood that various alternatives to the embodiments of the present invention described herein may be employed in practicing the present invention. It is intended that the following claims define the scope of the present invention and that methods and structures within the scope of these claims and their equivalents be covered thereby. The present invention is not limited to the embodiments described above, but is capable of modification within the scope of the appended claims. Those skilled in the art will recognize, or be able to ascertain using no more than routine experimentation, many equivalents of the specific embodiments of the present invention described herein.

What is claimed is:
1. A method for treating a lipid storage disease in a subject in need thereof comprising administering to said subject an effective amount of a compound of Formula 1b:

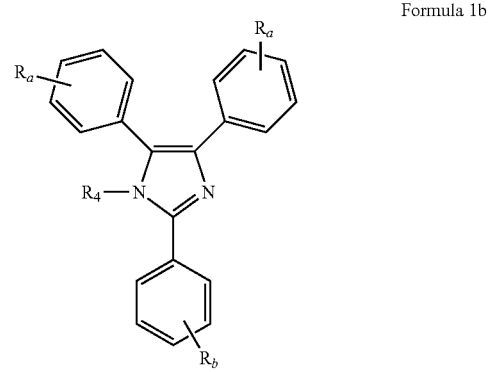

Formula 1b wherein each instance of $R_a$ is independently $C_{1-6}$ alkylamino, di($C_{1-6}$ alkyl)amino, substituted $C_{1-6}$ alkylamino, di(substituted $C_{1-6}$ alkyl)amino, $C_{3-6}$ alkenylamino, di($C_{3-6}$ alkenyl)amino, substituted $C_{3-6}$ alkenylamino, or di(substituted $C_{3-6}$ alkenyl)amino; and $R_b$ is HO—$C_{1-6}$ alkyl-$C_{2-6}$ alkenyl, $R_7$—O—$C_{1-6}$ alkyl-$C_{2-6}$ alkenyl, $R_7$NH—$C_{1-6}$ alkyl-$C_{2-6}$ alkenyl, $R_6R_7$N—$C_{1-6}$ alkyl-$C_{2-6}$ alkenyl, $R_7$NH—C(O)—O—$C_{1-6}$ alkyl-$C_{2-6}$ alkenyl, $R_6R_7$N—C(O)—O—$C_{1-6}$ alkyl-$C_{2-6}$ alkenyl, $R_7$O—C(O)—O—$C_{1-6}$ alkyl-$C_{2-6}$ alkenyl, or $R_7$—C(O)—O—$C_{1-6}$ alkyl-$C_{2-6}$ alkenyl;

wherein $R_6$ and $R_7$ are independently selected from the group consisting of $C_{1-6}$ alkyl, phenyl-$C_{1-6}$ alkyl, $C_{1-6}$ alkoxycarbonylmethyleneoxy, hydroxy-$C_{2-6}$ alkyl, $C_{1-6}$ alkyloxy-$C_{2-6}$ alkyl, amino-$C_{2-6}$ alkyl, $C_{1-6}$ alkylamino-$C_{2-6}$ alkyl, di($C_{1-6}$ alkyl)amino-$C_{2-6}$ alkyl, $C_{1-6}$ alkylthio-$C_{2-6}$ alkyl, substituted $C_{1-6}$ alkoxy-$C_{2-6}$ alkyl, substituted $C_{1-6}$ alkylamino-$C_{2-6}$ alkyl, di(substituted $C_{1-6}$ alkyl)amino-$C_{2-6}$ alkyl, substituted $C_{1-6}$ alkylthio-$C_{2-6}$ alkyl, wherein the substituents are selected from the group consisting of pyrrolidino, piperidino, morpholino, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy-$C_{3-6}$ alkenyl)piperazino, 4-N—($C_{1-6}$ alkylamino-$C_{1-6}$ alkyl)piperazino, 4-N—($C_{1-6}$ alkylamino-$C_{3-6}$ alkenyl)piperazino, imidazolyl, oxazolyl, and thiazolyl; and $R_4$ is selected from the group consisting of:
 (i) hydrogen;
 (ii) substituted $C_{1-11}$ alkyl or $C_{2-11}$ alkenyl wherein the substituents are independently selected from the group consisting of:
  (a) hydrogen, hydroxy, $C_{1-6}$ alkyloxy, $C_{1-6}$ alkylthio, $C_{1-6}$ alkylamino, phenyl-$C_{1-6}$ alkylamino, or $C_{1-6}$ alkoxycarbonyl;
  (b) substituted $C_{1-6}$ alkyloxy, $C_{3-6}$ alkenyloxy, or substituted $C_{3-6}$ alkenyloxy;

(c) di($C_{1-6}$ alkyl)amino, substituted $C_{1-6}$ alkyl-amino, di(substituted $C_{1-6}$ alkyl)amino, $C_{3-6}$ alkenyl-amino, di($C_{3-6}$ alkenyl)amino, substituted $C_{3-6}$ alkenyl-amino, or di(substituted $C_{3-6}$ alkenyl)amino; and (d) pyrrolidino, piperidino, morpholino, imidazolyl, substituted imidazolyl, piperazino, 4-N—$C_{1-6}$ alkylpiperazino, 4-N—$C_{3-6}$ alkenylpiperazino, 4-N—($C_{1-6}$ alkoxy $C_{1-6}$ alkyl)piperazino, 4-N—($C_{1-6}$ alkoxy $C_{3-6}$ alkenyl)piperazino, 4-N—($C_{1-6}$ alkylamino $C_{1-6}$ alkyl)piperazino, or 4-N—($C_{1-6}$ alkylamino $C_{3-6}$ alkenyl)piperazino; and (iii) aryl $C_{0-11}$ alkyl wherein the aryl group is selected from phenyl, imidazolyl, furyl, and thienyl, wherein said disease is not Fabry's disease.

2. The method of claim 1, wherein the compound of Formula 1b has the following formula (Formula 2):

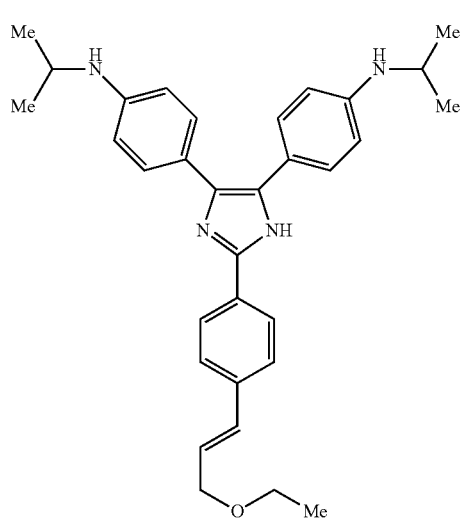

Formula 2 in the form of a free compound or as its pharmaceutically-acceptable pro-drug, metabolite, analogue, derivative, solvate or salt.

3. The method of claim 1 wherein the disease is characterized by a defect in glycosphingolipid synthesis.

4. The method of claim 3, wherein the glycosphingolipid is a neutral glycosphingolipid.

5. The method of claim 1 wherein the disease is characterized by a defect in ceramide synthesis.

6. The method of claim 1 wherein the disease is Gaucher's disease.

7. The method of claim 1 wherein the disease is characterized by a defect in ganglioside synthesis in the subject.

8. The method of claim 7, wherein the ganglioside is a GM1 ganglioside.

9. The method of claim 7, wherein the ganglioside is a GM2 ganglioside.

10. The method of claim 9, wherein the disease is Tay Sach's disease.

11. The method of claim 9, wherein the disease is Sandhoff's disease.

12. The method of claim 7, wherein the disease is cystic fibrosis.

13. The method of claim 1 further comprising administering a second compound effective to treat the lipid storage disease.

14. The method of claim 13 wherein the second compound is a glucosylceramide synthase inhibitor.

15. The method of claim 14, wherein the glucosylceramide synthase inhibitor is miglustat.

16. The method of claim 13 wherein the second compound is an enzyme administered as enzyme replacement therapy.

17. The method of claim 13 wherein the second compound is a pharmacological chaperone which binds to an enzyme and promotes trafficking of the enzyme from the endoplasmic reticulum to the lysosome.

18. The method of claim 1, wherein $R_4$ is hydrogen.

19. The method of claim 3, wherein the compound of Formula 1b has the following formula (Formula 2):

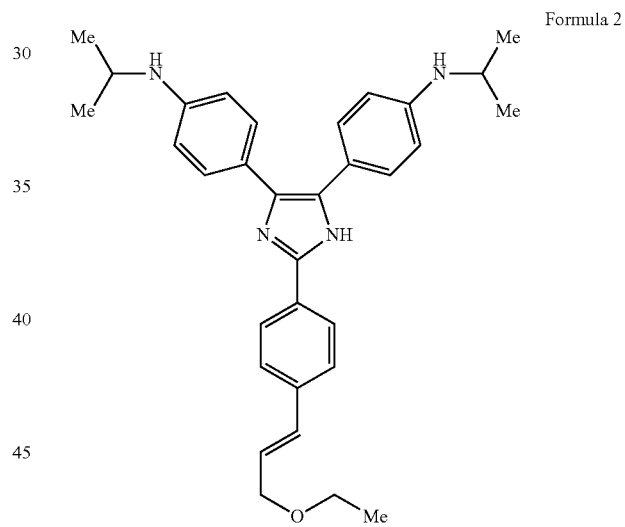

Formula 2 in the form of a free compound or as its pharmaceutically-acceptable pro-drug, metabolite, analogue, derivative, solvate or salt.

* * * * *